(12) United States Patent
Eicher et al.

(10) Patent No.: US 12,390,605 B2
(45) Date of Patent: Aug. 19, 2025

(54) DEVICE FOR PUTTING AN INHALER INTO A TRIGGERING-READY STATE

(71) Applicant: Boehringer Ingelheim International GmbH, Ingelheim am Rhein (DE)

(72) Inventors: Joachim Carl Herbert Eicher, Ingelheim Am Rhein (DE); Andree Jung, Ingelheim Am Rhein (DE)

(73) Assignee: BOEHRINGER INGELHEIM INTERNATIONAL GMBH, Ingelheim am Rhein (DE)

( * ) Notice: Subject to any disclaimer, the term of this patent is extended or adjusted under 35 U.S.C. 154(b) by 1324 days.

(21) Appl. No.: 16/772,521

(22) PCT Filed: Dec. 14, 2018

(86) PCT No.: PCT/EP2018/084930
§ 371 (c)(1),
(2) Date: Jun. 12, 2020

(87) PCT Pub. No.: WO2019/121386
PCT Pub. Date: Jun. 27, 2019

(65) Prior Publication Data
US 2020/0384216 A1 Dec. 10, 2020

(30) Foreign Application Priority Data
Dec. 18, 2017 (EP) .................................. 17208064

(51) Int. Cl.
*A61M 15/00* (2006.01)
*B05B 11/10* (2023.01)

(52) U.S. Cl.
CPC ...... *A61M 15/009* (2013.01); *A61M 15/0068* (2014.02); *B05B 11/1091* (2023.01);
(Continued)

(58) Field of Classification Search
CPC ............ A61M 15/009; A61M 15/0068; A61M 2205/18; A61M 2205/3584;
(Continued)

(56) References Cited

U.S. PATENT DOCUMENTS

| 5,497,764 A | 3/1996 | Ritson |
| 5,833,088 A | 11/1998 | Kladders |

(Continued)

FOREIGN PATENT DOCUMENTS

| CA | 2997649 A1 | 4/2017 |
| WO | 9200770 A1 | 1/1992 |

(Continued)

OTHER PUBLICATIONS

International Search Report for corresponding PCT Application No. PCT/EP2018/084930, 3 pages, dated Mar. 4, 2019.

*Primary Examiner* — Justine R Yu
*Assistant Examiner* — Matthew R Moon
(74) *Attorney, Agent, or Firm* — Calderon Safran & Wright P.C.; David S. Safran

(57) ABSTRACT

A device is designed to put the inhaler into a triggering-ready state by adding energy to a stored energy source of the inhaler. The inhaler can be inserted into the device and/or mechanically coupled to the device in order to put the inhaler into the triggering-ready state.

19 Claims, 9 Drawing Sheets

(52) U.S. Cl.
CPC . *A61M 2205/18* (2013.01); *A61M 2205/3584* (2013.01); *A61M 2205/502* (2013.01); *A61M 2205/582* (2013.01); *A61M 2205/587* (2013.01); *A61M 2205/8206* (2013.01); *A61M 2209/086* (2013.01)

(58) Field of Classification Search
CPC ...... A61M 2205/502; A61M 2205/582; A61M 2205/587; A61M 2205/8206; A61M 2209/086; A61M 15/0065; A61M 2209/02; A61M 2209/04; A61M 15/00; B05B 11/1091
See application file for complete search history.

(56) References Cited

U.S. PATENT DOCUMENTS

| | | |
|---|---|---|
| 7,849,851 B2 | 12/2010 | Zierenberg |
| 2004/0231667 A1* | 11/2004 | Horton ................ A61M 15/008 128/202.13 |
| 2005/0247305 A1 | 11/2005 | Zierenberg |
| 2010/0012115 A1* | 1/2010 | Bacon ............... A61M 15/0065 128/200.23 |
| 2015/0041558 A1* | 2/2015 | Besseler ............. B05B 11/0038 239/302 |
| 2019/0113418 A1 | 4/2019 | Eicher |

FOREIGN PATENT DOCUMENTS

| | | |
|---|---|---|
| WO | 9606011 A2 | 2/1996 |
| WO | 9720590 A1 | 6/1997 |
| WO | 2004024340 A1 | 3/2004 |
| WO | 2005080001 A1 | 9/2005 |
| WO | 2009047173 A2 | 4/2009 |
| WO | 2011157561 A1 | 12/2011 |
| WO | 2017060238 A1 | 10/2016 |
| WO | WO-2017060328 A1 * | 4/2017 ........ A61M 15/0065 |

* cited by examiner

DEVICE FOR PUTTING AN INHALER INTO A TRIGGERING-READY STATE

BACKGROUND

The present invention relates to a device for putting an inhaler into a triggering-ready state by adding energy to an energy store of the inhaler, and to a system with a device and an inhaler.

A device according to the invention is designed to add energy to a preferably mechanical energy store of an inhaler, in particular to tension a spring or drive spring. The inhaler is preferably put into a triggering-ready state by adding energy to the energy store.

An "inhaler" within the meaning of the following invention is preferably designed to atomise a substance, for example a powder or a fluid, in particular a pharmaceutical formulation, or to convert it into an aerosol. The generated aerosol can then be breathed in or inhaled by a user or patient, in particular to treat an illness. The inhaler is preferably a portable or mobile device.

Within the meaning of the present invention an inhaler preferably comprises a container as a reservoir for the substance to be atomised, preferably wherein the container for dispensing the substance, in particular the fluid, is movable—preferably axially—relative to a housing part. Particularly preferably an inhaler comprises an energy store, in particular configured in the form of a spring, wherein the substance to be atomised is pressurised by release of energy from the energy store or by detensioning the spring, and is atomised via a nozzle or discharge nozzle or is dispensed as an inhalable aerosol. Furthermore, particularly preferably energy can be added to the energy store or the spring can be tensioned by a relative movement, in particular twisting, of two housing parts with respect to one another. Such an inhaler is known for example from WO 2009/047173 A2.

A "triggering-ready state" of an inhaler is a state in which a triggering or atomisation of the inhaler can be effected directly, for example by actuating a triggering element such as a triggering mechanism to trigger a mechanical pressure generation. In particular, a triggering-ready state is a state in which no further preparatory steps or measures are necessary for the triggering or atomisation. A triggering-ready state is particularly preferably a state in which energy for a pressure generator of the inhaler is provided by addition of energy to an energy store or by tensioning a spring, in order to atomise the substance to be atomised, in particular a fluid.

When atomising a substance or a fluid, in particular a liquid pharmaceutical formulation, by means of an inhaler of the type mentioned in the introduction, an amount of active ingredient defined as precisely as possible should be converted into an aerosol for inhalation. The aerosol produced in this way should be characterised by a small mean value of the droplet size with a narrow droplet size distribution and a small momentum or a low propagation velocity. The droplets produced in this way preferably have a droplet diameter of less than 5 micrometres, in particular between 2 micrometres and 5 micrometres, since droplets of this size are deposited in a suitable manner in pulmonary systems during inhalation.

The term "fluid" within the meaning of the present invention should preferably be understood and interpreted broadly. The fluid is preferably a liquid. In particular, the term "fluid" also includes active ingredient solutions, dispersions, suspensions or the like.

The term "aerosol" in the present invention should preferably be understood as a cloud-like or mist-like accumulation of a large number of liquid or solid airborne particles of a substance preferably atomised by means of an inhaler, preferably in which the airborne particles have a low velocity and/or at least substantially non-directional directions of movement. An "aerosol" can for example comprise or form a conically shaped particle cloud, in particular where the main direction of propagation of the particle cloud corresponds at least substantially to the main exit direction or exit momentum direction.

In the inhaler known from WO 2009/047173 A2 a triggering or atomisation must first of all be prepared for by tensioning a drive spring of the inhaler. The subsequent actuation of a triggering push button then causes an atomisation or generation of an aerosol.

To add energy to the energy store, here therefore particularly to tension the drive spring, a certain manipulation force and—in particular to rotate the housing parts relative to one another by 180° in one continuous movement—motor coordination and in particular the use of both hands are required, which can be stressful or problematic especially for older or geriatric, weakened and/or ill users of the inhaler as well as patients. In certain circumstances it may be the case that these people can put the inhaler into a triggering-ready state only with great effort without any aids, or manually by adding energy to the energy store, and/or find it difficult or problematic to add energy to the energy store manually. This may mean that a required medication that has to be inhaled by means of the inhaler cannot or will not be taken without the help of carers.

A system is known from WO 2017/060328 A1 for the automated checking of the functional capability of an inhaler, as part of a production line. The system is envisaged for use in a series production process or is integrated in a manufacturing process of the inhaler and optionally comprises a tensioning device for tensioning an inhaler. The system and the tensioning device are not portable and in particular cannot be transported manually or without aids by a user or patient. Even if an inhaler too is tensioned, it is not possible directly to isolate this function from the overall system context, so that WO 2017/060328 A1 should be regarded as remote prior art.

SUMMARY

Against this background the object of the present invention is to provide a portable device and a system with which an inhaler can be converted, in particular by adding energy to an energy store or by tensioning a spring, in a force-saving, comfortable and/or reliable manner, to a triggering-ready state.

A device in the meaning of the present invention preferably serves to convert an inhaler into a triggering-ready state by adding energy to an energy store of the inhaler, in particular by tensioning a spring.

A device according to the invention is in particular a mobile, independent, battery-operated or storage battery-operated and/or portable device or a device that is not permanently installed in one place.

The device is preferably designed in such a way that an inhaler can be inserted into the device and/or mechanically coupled to the device in order to put the inhaler into the triggering-ready state.

The device preferably comprises a motor drive for moving two housing parts of an inhaler inserted into and/or coupled to the device relative to one another, wherein by the movement of the housing parts relative to one another energy can be added to the energy store of the inhaler and the spring of the inhaler can be tensioned. A manual tensioning by a user can therefore be dispensed with, thereby enabling an easier and safer use of the inhaler. In addition a complete or sufficient tensioning of the spring can be ensured, in particular wherein manual influences are avoided during tensioning.

The motor drive furthermore allows a one-handed operation of the device and/or the inhaler. In particular, by using the device the two-handed manual tensioning of the spring or addition of energy to the energy store is dispensed with. This also has the advantage that a possible (manual) incorrect operation of the inhaler is avoided.

According to a further, also independently realisable aspect, the device comprises two coupling devices, wherein the coupling devices can each preferably be mechanically coupled to one of two housing parts of the inhaler, so that the two housing parts can be moved relative to one another with the coupling devices, whereby due to the movement of the housing parts relative to one another energy can be added to the energy store or the spring can be tensioned. The addition of energy or the tensioning is thus facilitated, in particular can be automated, and is thus effected automatically by the device.

The device and/or the drive are preferably designed so as to twist or rotate the housing parts relative one another. The device and/or the drive are particularly preferably designed to rotate the housing parts relative to one another by more than 90° and/or at most 360°, in particular by 180°. An easy and reliable addition of energy to the energy store is thus enabled.

The device and/or the drive are preferably designed so that the force or energy introduced by them is limited. Thus, a device for the relative rotation of housing parts with respect to one another is preferably designed to stop further force being applied when a predetermined maximum torque is reached, the maximum torque preferably being 0.5 Nm, 0.6 Nm or 0.8 Nm. In this way damage or destruction of the inhaler, the device and/or the drive can be avoided.

The drive preferably comprises an electric motor and/or a gear mechanism. A simple, safe and reliable addition of energy to the energy store is thereby enabled and the operation of the inhaler and/or the device is facilitated.

In a preferred embodiment the device comprises a sensor, which is designed to detect the insertion of the inhaler, the coupling of the inhaler and/or its state or tension state. A reliable tensioning of the inhaler is thus possible and/or an unnecessary tensioning of the inhaler can be avoided.

The expression "tensioning of the inhaler" is used as a short form for "addition of energy to the energy store of the inhaler" and should be understood in particular as a synonym.

The device preferably comprises a controller, which is designed to detect together with the aforementioned sensor the insertion and/or coupling of the inhaler and its state or tension state. Particularly preferably the controller is furthermore designed to control the drive depending on this detection, preferably so that the inhaler is automatically put in the triggering-ready state by adding energy to the energy store.

The inhaler can therefore be automatically put into and/or held in the triggering-ready state by the device, in particular on insertion and/or by touching a push button or by actuating a corresponding switch. This is conducive to an easier operation, since a patient or user of the inhaler can therefore after using the inhaler insert this, in particular manually, into the device, whereby the device automatically restores the inhaler to the triggering-ready state or maintains it in this state. For the next inhalation or delivery or triggering the patient or user simply has to remove the inhaler from the device and can then directly and without further preparation trigger the inhaler, atomise the substance contained in the container, and/or inhale the generated aerosol. A simple and safe operation is thereby realised.

The device can comprise a communication device for the preferably wireless communication with the inhaler and/or an external system. If necessary the communication device can be designed in several parts and is preferably configured to send and/or receive information on the state of the inhaler and/or its use. The operation of the inhaler and/or the device can thus be facilitated and made less complicated.

The device preferably comprises a preferably electronically operated output device, in particular a display and/or a loudspeaker, for the preferably optical and/or acoustical output of information on the condition of the inhaler and/or its use. This enables an easier and/or safe operation of the inhaler and/or the device.

It is preferred that the device comprises an energy supply device for supplying the device with (electrical) energy. The device or energy supply device is preferably designed for connection to a power supply network. Particularly preferably the device or energy supply device comprises a preferably rechargeable (electrical) energy store, in particular a storage battery. This is conducive to a reliable and/or at least temporary function of the device independent of the power supply network.

Alternatively or additionally, the device preferably comprises a charging device for charging an energy store of the inhaler. This is conducive to a reliable and/or mains-independent function of the inhaler.

Particularly preferably the device comprises a receptacle for inserting and/or holding the inhaler. A simple operation or use of the device is thereby enabled and the device can furthermore be used for storing the inhaler.

Most particularly preferably the device is designed so that, by in particular manual insertion of the inhaler into the receptacle, for example by a patient or user, the drive is connected to one of the (two) housing parts and the other housing part is connected—preferably in a positive engagement manner—to the receptacle, so that the housing part connected to the drive is movable, preferably rotatable, relative to the other housing part and/or the other housing part is held immovably and/or preferably in a rotation-proof manner in the receptacle—at least during the addition of energy or tensioning. A reliable addition of energy to the energy store and tensioning of the spring is thereby enabled.

According to a further aspect the present invention relates to a system with a device and an inhaler, wherein by means of the device energy can be added to an energy store of the inhaler by a relative movement, in particular twisting, of two housing parts of the inhaler relative to one another, or a spring can be tensioned.

The inhaler preferably comprises a counter for counting uses of the inhaler. This is conducive to the safe use of the inhaler or system. A user or patient can thus easily check whether he/she is using the inhaler or the system as desired or prescribed. In particular, he/she can thus ensure or check whether a prescribed number of doses of a medication is or has been taken. The counter can be designed electronically or mechanically.

The device and the inhaler preferably each have a communication device for preferably wireless communication, so that a data connection can be established between the communication devices of the device and the inhaler.

Preferably the counter can be connected to the device via a data connection. The device in turn is preferably designed to receive, output and/or transmit the counter reading to an external device different from the inhaler. Here the device serves in particular as a coupling element or "gateway" for providing usage information concerning the inhaler. An easier operation and/or reliable functioning of the system is thereby enabled.

The inhaler preferably comprises a preferably mechanical pressure generator for conveying and atomising a fluid, wherein the fluid is conveyed to a pressure chamber of the pressure generator when energy is added to the energy store or the spring is tensioned, and/or wherein by a detensioning of the energy storage system or spring the fluid is pressurised and dispensed through a nozzle as an inhalable aerosol. An aerosol of the type described in the introduction can thus be generated in a simple and reliable manner. With inhalers of this type it is particularly advantageous conveniently to generate the necessary energy of the energy store or tension of the spring by means of the device. The device can however also be combined with other inhalers.

BRIEF DESCRIPTION OF THE DRAWING

Further aspects, features, properties and advantages of the present invention follow from the claims and the following description of preferred embodiments with reference to the drawings, in which:

DETAILED DESCRIPTION OF THE EMBODIMENTS

Figure 1:
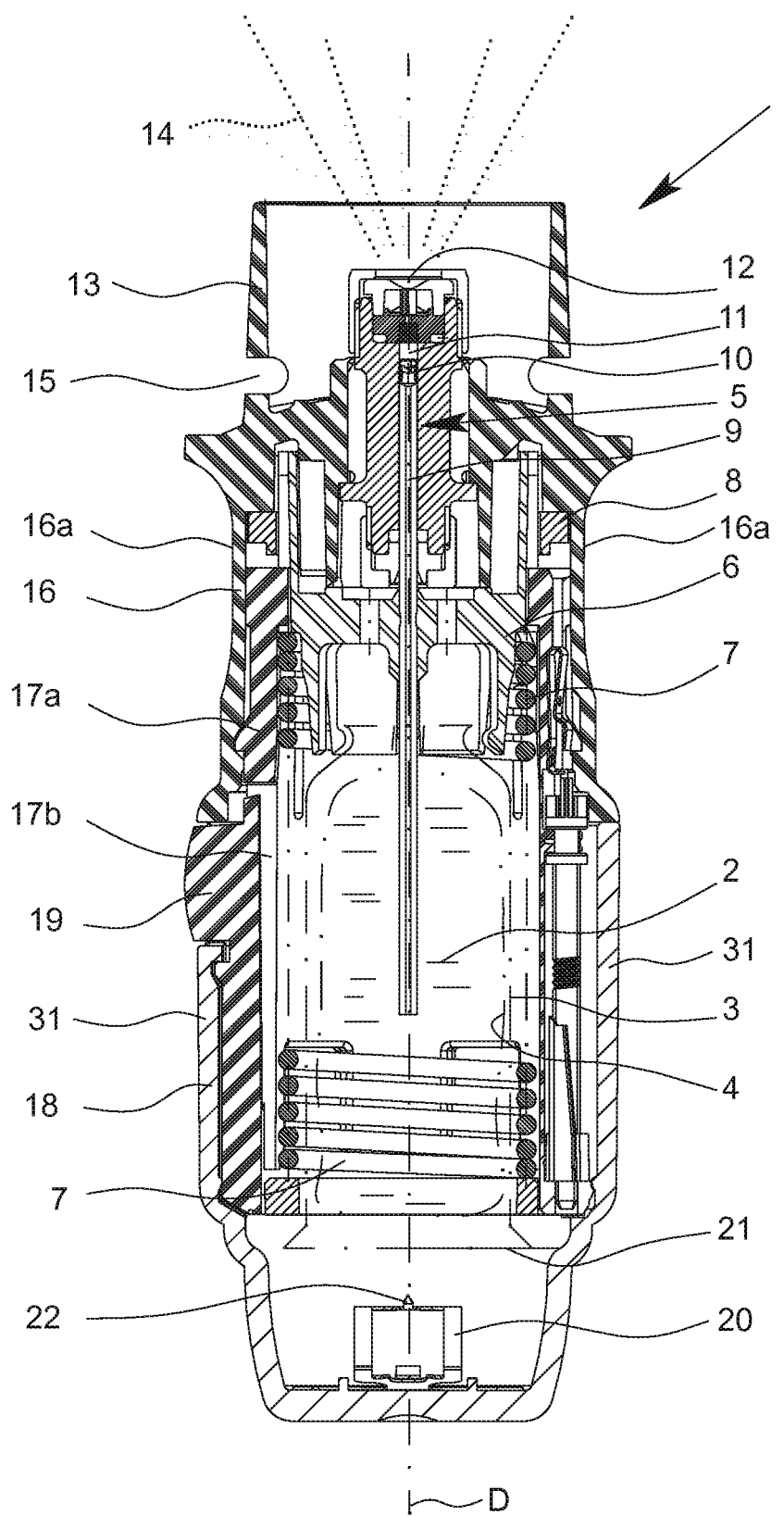
FIG. 1 is a schematic section of an inhaler in the non-tensioned state.

In the figures, which are partially not to scale and only schematic, the same reference numerals are used for the same or similar parts, wherein corresponding or comparable properties and advantages can be achieved, even if a repeated description is omitted for the sake of clarity.

A particularly preferred embodiment of an inhaler 1 is first described hereinafter, which can be put into a triggering-ready state with a proposed device 23. The device 23 itself will then be discussed.

Figure 2:
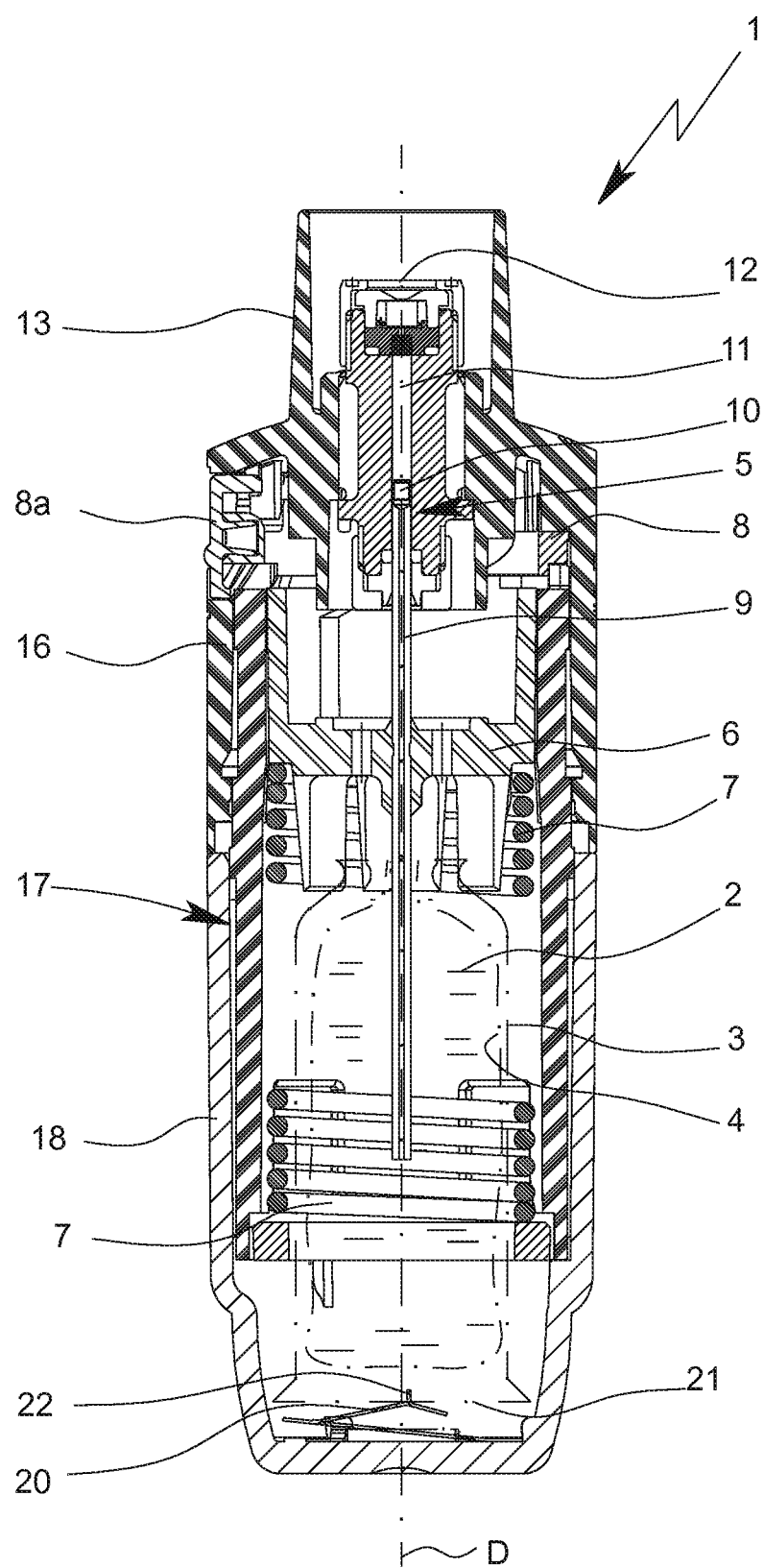
FIG. 2 is a schematic section of the inhaler, rotated by 90° compared to FIG. 1, in the tensioned state.
Figure 3:
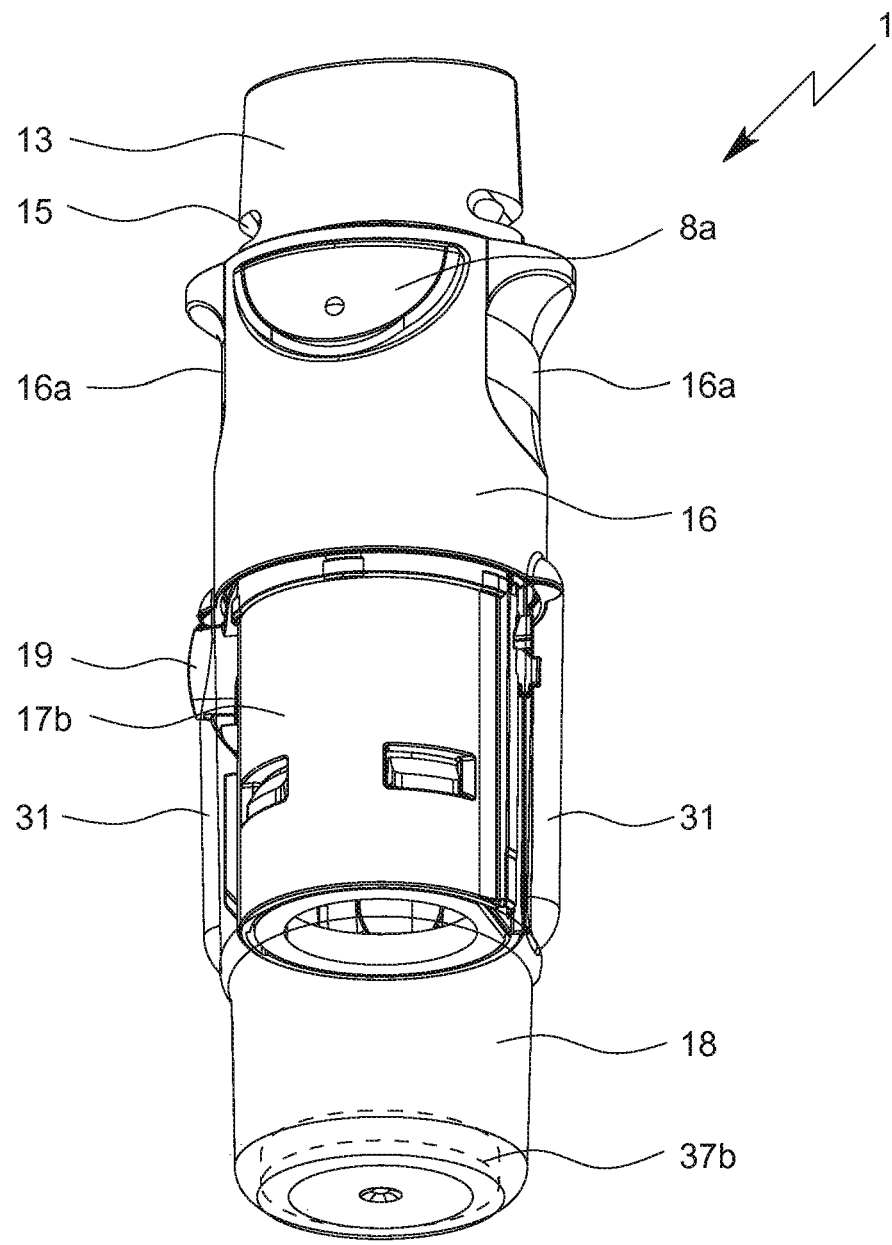
FIG. 3 is an external perspective view of an inhaler.

FIGS. 1 to 3 show an inhaler 1 for atomising a fluid 2, in particular a highly effective medicament or the like, as is used for example in the device 23 according to the invention and/or is coupled thereto.

FIGS. 1 and 2 show the inhaler 1 in a schematic illustration in the non-triggering-ready or non-tensioned state (FIG. 1) and in the triggering-ready or tensioned state (FIG. 2). The terms "non-tensioned" and "tensioned state" denote in this connection the state of the energy store 7 contained in the inhaler 1, preferably formed by a spring or drive spring. In the "non-tensioned state" (FIG. 1) the inhaler 1 is therefore not triggering-ready and in the "tensioned state" (FIG. 2) the inhaler 1 is triggering-ready. The tensioned or non-tensioned state or tension state of the inhaler 1 is therefore in particular the (tension) state of the energy store 7 or the drive spring of the inhaler 1.

The energy store 7 and the drive spring are preferably incorporated in the inhaler 1 in such a way that the energy store 7 and/or the drive spring are already pre-tensioned or partially compressed. The non-tensioned state is preferably a state in which the inhaler is not triggering-ready, but the energy store 7 and/or the drive spring are however already pre-tensioned or partially compressed.

The term "tensioning" of the spring or drive spring is understood in particular to mean a deflection of the spring or a change of the length of the spring, in which a spring force or restoring force is generated and/or increased. In other words, by tensioning the spring energy, in particular tensioning energy, is added to the spring and stored (in particular as potential energy) in this. Basically the term "tensioning" of the spring includes a lengthening or stretching of the spring as well as a shortening or compression of the spring. In the preferred embodiment of the inhaler 1 the spring and the energy store 7 are preferably tensioned by being forced together and/or compressed.

The inhaler 1 is designed in particular as a portable, carriable and/or mobile inhaler 1.

On atomising the substance or the fluid 2, preferably a liquid, in particular a medicament, an aerosol 14 is preferably formed by means of the inhaler 1, in particular wherein the aerosol 14 can be breathed in or inhaled by a user (not shown).

Inhalation normally takes place at least once a day, in particular several times a day, preferably at predetermined time intervals, for example depending on the patient's illness.

The aerosol 14 is preferably a particle-air mixture with solid and/or liquid particles, which are particularly preferably respirable, and therefore particularly at least in some cases or on average are less than 5 μm in diameter.

The inhaler 1 is preferably propellant-free, and therefore preferably works without propellant gas. Instead, the inhaler 1 preferably works with a (mechanical) mechanism for generating the aerosol 14. In particular in this connection it is a mechanically operated pump, which pressurises the fluid 2, the aerosol 14 thereby being generated. In principle however the inhaler 1 can also be driven in a different, preferably mechanical, way.

The inhaler 1 comprises a preferably insertable and preferably replaceable container 3 with the fluid 2. The container 3 preferably forms a reservoir for the fluid 2 to be atomised. In FIG. 3 the inhaler 1 is shown without the container 3.

The container 3 preferably contains a sufficient amount of fluid 2 or active ingredient so as to be able to provide up to 200 dosing units for example, accordingly to enable up to 200 atomisations or applications for example. A typical container 3, as disclosed in WO 96/06011 A2, has a volume of ca. 2 ml to 10 ml.

The container 3 is preferably designed at least substantially cylindrical or cartridge-like, and after the inhaler 1 has been opened can be inserted into the latter from below and, if necessary, replaced.

The container 3 is preferably formed at least substantially rigid. The container 3 is particularly preferably made of plastic, in particular a thermoplastic, most particularly preferably polypropylene. The container 3 preferably has a flat surface at its base or the container 3 has a flat container base 21.

Optionally the container 3 comprises a metallic and/or reflective outer casing and/or a metallic and/or reflective container base 21 or a metallic and/or reflective (outer) coating on the container base 21.

The fluid 2 is preferably contained in the container 3 in a fluid space 4 formed by a collapsible bag.

The inhaler 1 preferably furthermore comprises a preferably mechanical pressure generator 5 for conveying and atomising the fluid 2, in particular in each case in a predetermined, optionally adjustable, dosing amount.

The pressure generator 5 preferably comprises an energy store 7—only partially shown in the illustrated example—for driving the pressure generator 5. The energy store 7 is in this case preferably designed to store energy and release it to the pressure generator 5, so that the pressure generator 5 pressurises the fluid 2, whereby the aerosol is formed from the fluid 2. The pressure generator 5 is thus driven by the energy store 7 or by the energy made available by the energy store 7.

The energy store 7 is preferably designed as a spring or coil spring. The addition of energy to the energy store 7 or the tensioning of the spring is effected in particular by compressing the energy store 7 or the spring.

The pressure generator 5 preferably comprises a holder 6 for the container 3, the associated, only partially illustrated energy store 7 with a locking element 8 for the detensioning, which can be operated manually—directly or preferably via a release push button 8a—a delivery tube 9 with a non-return valve 10, a pressure chamber 11 and a discharge nozzle 12 in the region of a mouthpiece 13. The container 3 is preferably fixed via the holder 6, in particular in a non-locking manner, in the holder 1 in such a way that the delivery tube 9 dips into in the container 3. The holder 6 can be designed in such a way that the container 3 can be detached and replaced.

During the axial tensioning of the energy store 7 or the spring, the holder 6 with the container 3 and the delivery tube 9 is moved downwards in the illustrations and the fluid 2 is aspirated from the container 3 via the non-return valve 10 into the pressure chamber 11 of the pressure generator 5.

In the subsequent detensioning of the energy store 7 or the spring after actuation of the locking element 8 the fluid 2 in the pressure chamber 11 is pressurised, in which the delivery tube 9 with its now closed non-return valve 10 is moved up again by detenionsing the energy store 7 or the spring, and now serves as a pressure piston. This pressure forces the fluid 2 through the discharge nozzle 12, whereby it is atomised into the aerosol 14, as indicated in FIG. 1.

The delivery tube 9 is preferably fixed in the position of use in relation to the container 3, in particular via the holder 6. It is therefore particularly envisaged that an (axial) movement of the delivery tube 9 corresponds to an (axial) movement of the container 3.

If the delivery tube 9 or the non-return valve 10 functions as a pressure piston, a movement of the delivery tube 9 or the container 3 corresponds to a volume displaced in the pressure chamber 11 or a discharged or dispensable amount of fluid.

A user or patient, not shown, can inhale the atomised fluid 2 or the aerosol 14, preferably wherein supply air can be aspirated into the mouthpiece 13 via at least one supply air opening 15.

The inhaler 1 preferably comprises mutually rotatable housing parts 16, 17, 18. Furthermore, the inhaler 1 is preferably designed to add energy to the energy store 7 by turning the housing parts 16, 17, 18 relative to one another or to tension the spring, in particular therefore to compress the spring or drive spring.

In the illustrated example the inhaler 1 preferably comprises a housing part 16 and an inner part 17 or inner housing part (FIG. 2) rotatable relative thereto, with an upper part 17a and a lower part 17b (FIG. 1). A housing lower part or (lower) housing part 18 or a cap is preferably detachably fastened, in particular mounted, on the inner part, preferably by means of a holding element 19. Preferably the inner part 17 or inner housing part can be rotated manually by means of the lower housing part or housing part 18 relative to the housing part 16.

In FIG. 3 the housing part 18 is shown transparent. The housing part 18 is preferably transparent.

To insert and/or replace the container 3, the housing lower part or lower housing part 18 can preferably be detached from the inhaler 1. The container 3 can however also be non-replaceable or secured against removal.

The housing part 18 can be rotated relative to the housing part 16 or twisted relative to the housing part 16, preferably thereby entraining the lower part 17b of the inner part 17 in the illustration.

In particular the housing part 18 is arranged in a rotation-proof manner on the housing part or inner part 17, preferably by means of a positive connection.

The housing part or inner part 17 can therefore also be turned relative to the housing part 16 or twisted relative to the housing part 16.

The rotation of the housing parts 16, 17, 18 relative to one another or the relative twisting of the housing parts 16, 17, 18 with respect to one another occurs about an axis of rotation D of the inhaler 1. The axis of rotation D preferably forms a longitudinal axis, central axis and/or axis of symmetry of the inhaler 1.

Hereinafter an "axial" movement or direction is understood to mean a movement or direction that is identical to the axis of rotation D and/or extends parallel to or along this axis. Also, the term "radial" correspondingly refers in each case to the axis of rotation D.

By rotating the housing part 16 or the inner part 17 the energy store 7 and the spring are tensioned in the axial direction, in particular are forced together, via a drive (not shown) acting on the holder 6. With the tensioning the container 3 is preferably moved axially downwards until the container 3 adopts an end position indicated in FIG. 2 ("below" refers here to the position of the inhaler 1 shown in the figures, "below" on the inhaler 1 is here the end of the inhaler 1 remote from the mouthpiece). In this state the energy store 7 or the spring is tensioned or the inhaler 1 is in the tensioned state. During the atomisation process the container 3 is preferably retracted again (upwards, i.e. here in the direction of the mouthpiece 13) to its initial position by the energy store 7 or the spring.

The container 3 preferably executes an axial movement or lifting movement during the addition of energy or during the tensioning process or for the withdrawal of fluid and/or during the atomisation or delivery of the fluid 2.

In particular, the axial position of the container 3 is thus directly related to the state or tension state of the inhaler 1 or energy store 7 or the axial position of the container 3 is correlated with the state or tension state. In the non-tensioned state illustrated in FIG. 1 the container 3 is preferably in the upper axial position visible in FIG. 1. In the tensioned state the container 3 is preferably in the lower axial position visible in FIG. 2.

Preferably, when tensioning for the first time an axially acting spring 20 arranged in the housing part 18 abuts against the container base 21 and pierces the container 3 or a seal on the base side with a piercing element 22 for the initial venting. The spring 20 with the piercing element 22 is omitted from the illustration in FIG. 3.

The length of the inhaler 1 along the axis of rotation D is preferably between 6 cm and 13 cm, preferably about 10 cm, in particular measured from the bottom of the lower housing part 18 to the upper end of the mouthpiece 13. The length of the lower housing part 18 along the axis of rotation D is preferably between 3 cm and 7 cm, preferably about 5 cm.

The inhaler 1 preferably has perpendicular to the axis of rotation D at least substantially a round, in particular oval and/or circular, cross section. The diameter of the inhaler 1 perpendicular to the axis of rotation D is preferably between 2 cm and 5 cm, preferably about 3 cm. In the region of the flat portions 16a and/or the coupling sections 31 or through the flat portions 16a and/or the coupling sections 31 the cross section of the upper housing part 16 and/or of the lower housing part 18 can deviate at least in sections from a round shape or circular shape.

The inhaler 1 preferably comprises a blocking device, not illustrated in the figures, by means of which the further use or actuation of the inhaler 1 is prevented after a predetermined number of actuations. The blocking device is preferably designed as described in WO 2004/024340 A1. The blocking device preferably comprises a pre-tensioned leaf spring, which is arranged between the upper housing part 16 and the inner housing part 17 and, after a predetermined number of actuations of the inhaler 1, blocks a further actuation, in particular a rotation of the housing parts 16, 17, 18 relative to one another. The blocking takes place in particular in that the leaf spring is axially displaced by a plunger after a predetermined number of actuations, so that it engages in two recesses provided for this purpose in the housing parts 16 and 17 or is arranged between these recesses, and a further or renewed turning of the housing parts 16 and 17 relative to one another is thus blocked.

The housing parts 16, 17, 18 can when the blocking device is activated preferably be rotated relative to one another only by a large physical effort, although however the inhaler 1 itself is destroyed and/or becomes unusable. The energy or work required to twist the housing parts 16, 17, 18 when the blocking device is activated or the toque required for this purpose is preferably about 3 Nm.

Figure 4:
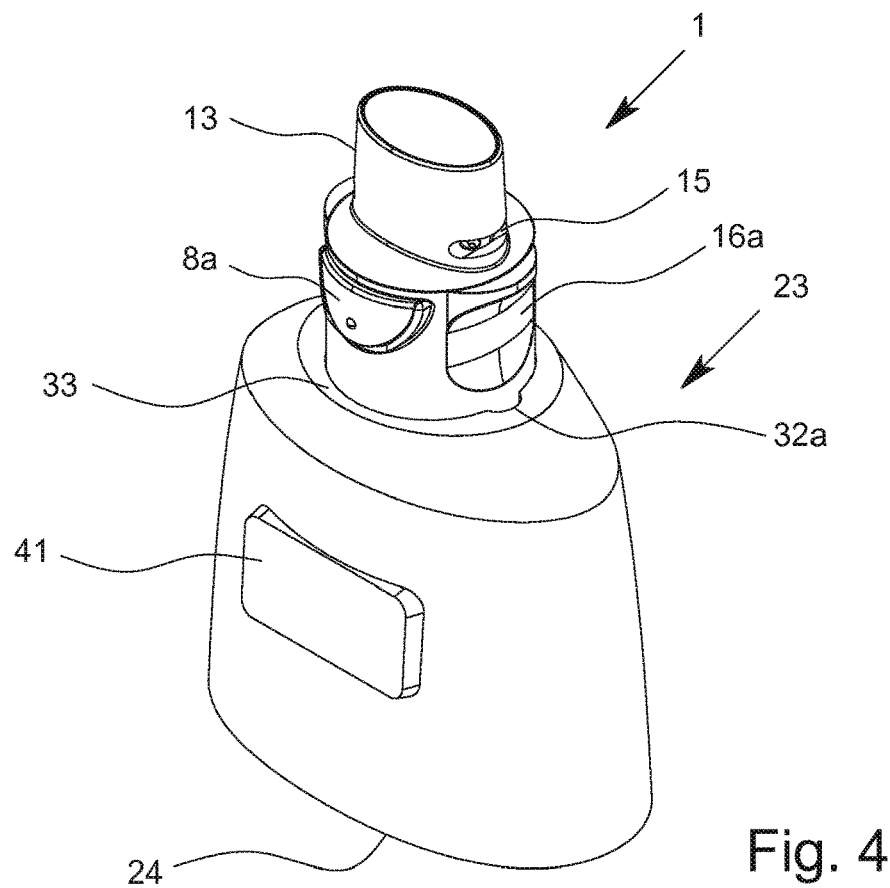
FIG. 4 is a perspective illustration of a proposed device according to a first embodiment with an inhaler inserted therein according to one of FIGS. 1 to 3.
Figure 5:
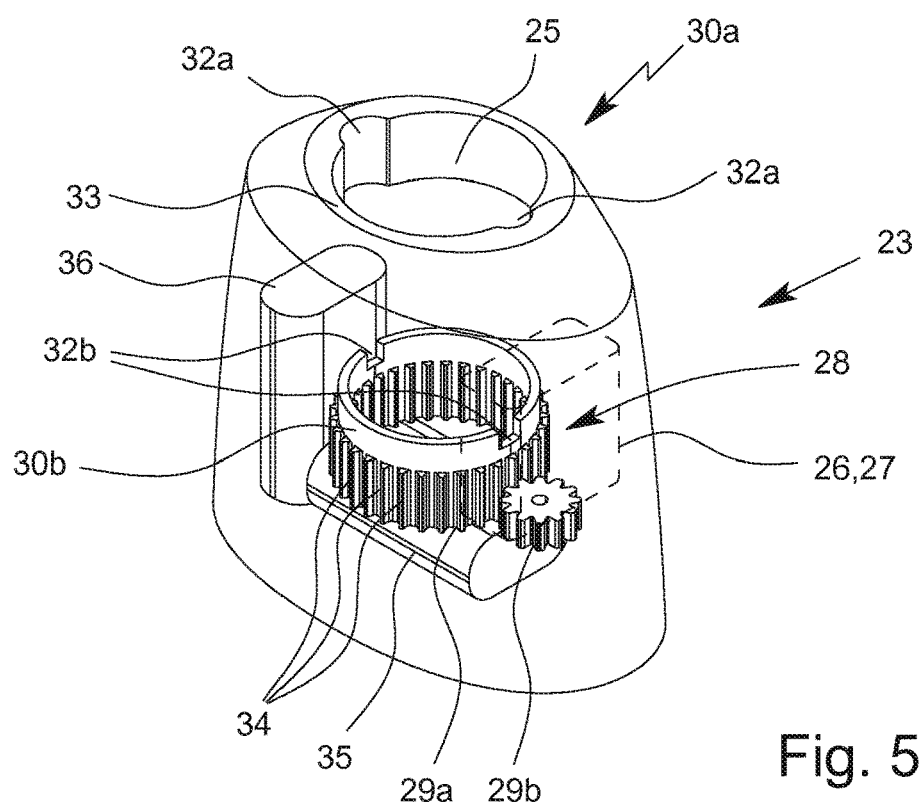
FIG. 5 is a schematic, partially transparent perspective illustration of the device according to FIG. 3, in which the interior of the device can be recognised.
Figure 6:
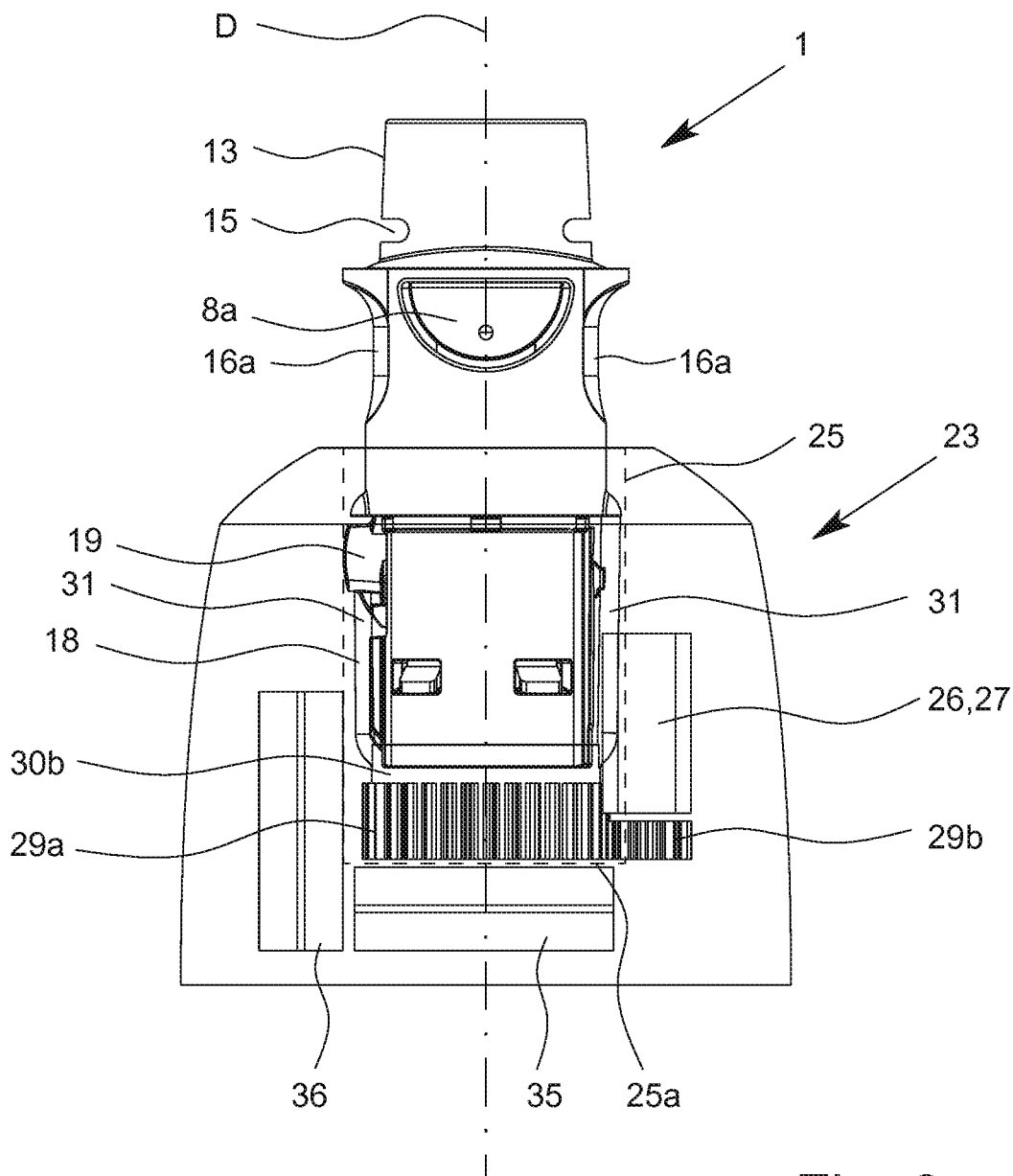
FIG. 6 is a schematic, partially transparent front view of the device according to FIGS. 4 and 5 with inserted inhaler.

FIGS. 4 to 6 show in various illustrations a device 23 according to the proposal for putting an inhaler into the triggering-ready state, in particular by adding energy to an energy store 7 or by tensioning a spring of the inhaler.

It should be noted that the device 23 described hereinafter can be realised basically independently, i.e. as a separate unit, from the previously described inhaler 1. In particular the device 23 is not limited to use with an individual inhaler 1, but can be used further with identically constructed devices (e.g. after the inhaler 1 is empty or has reached the end of its service life). Preferably the device 23 can be designed to be operated in conjunction with other inhalers that do not correspond or are not exactly structurally identical to the embodiment just described, wherein in particular the use of interchangeable inserts is also possible, so that the device 23 can be coupled by positive engagement to inhalers 1 that have differently designed coupling sections 31. In principle, individual aspects of the device 23 described hereinafter can be realised independently of one another and/or independently of the inhaler 1.

Preferably however the device 23 is designed to tension the spring of the previously described inhaler 1. The inhaler 1 and the device 23 preferably form a system, as shown in particular in FIG. 6.

The device 23 is preferably designed in such a way that the inhaler 1 does not have to be modified for use in connection with the device 23 and/or that the inhaler 1 can be used further without restriction, in particular can further be put manually into the triggering-ready state. This is particularly conducive to operating safety in the event of a malfunction or damage to the device 23.

The device 23 is preferably designed to be compact, portable, carriable and/or mobile. The device 23 is thus designed for example as a desktop or table-top device or as a handheld device. In particular the device 23 is designed as a type of docking station, table clamping station and/or charging station for the inhaler 1. The device 23 can for example be designed like a charging station for a mobile phone, a handset of a landline phone or an electric toothbrush.

In particular a portable, carriable and/or mobile device 23 is a device 23 that is meant for personal use by a patient or user and is not intended for industrial use or in the production and/or functional testing of the inhaler 1. The device 23 can preferably be transported manually and/or without tools or aids by a user or patient.

The device is preferably not installed, fastened or anchored fixedly at a location. In particular it is envisaged to use the device 23 for home use and/or not for industrial use.

In this connection the device 23 is preferably designed to be operated or operable independently of the mains network. In particular the device comprises for this purpose an energy store such as a storage battery, a battery or the like.

The device 23 preferably weighs less than 1 kg, in particular less than 0.5 kg. The device 23 preferably has a maximum extension of less than 25 cm, in particular less than 20 cm, particularly preferably less than 15 cm, and/or a volume of less than 2 dm$^3$, in particular less than 1 dm$^3$.

The device 23 can in particular be kept or stored on a table, shelf, sideboard, side table, bedside table and/or in a cupboard or the like.

It is preferably envisaged that the inhaler 1 is held, stored or kept permanently or for a long period of time in the device 23 and/or is removed or separated from the device 23 only for inhalation or some other use or actuation of the inhaler 1.

The device 23 is preferably designed to put the inhaler 1 in a triggering-ready state and/or to store, keep and/or hold the inhaler 1 in a triggering-ready state. Thus, a triggering or actuation of the inhaler 1 can take place quickly or immediately after its removal from the device 23. The device 23 is preferably designed not for triggering or not for an actuation of the triggering push button 8a.

Alternatively or additionally the device 23 can be designed to prevent and/or block a triggering of the inhaler 1, for example in that the triggering push button 8a is covered by a part or section of the device 23. This is not obligatory however.

It is also possible that the inhaler 1 can be triggered or the triggering push button 8a of the inhaler 1 can be actuated, in particular manually and/or by a user or patient, if the inhaler 1 is arranged in the device 23 or is inserted into the latter. The possibility of triggering the inhaler 1 while it is arranged in the device 23 or is inserted into the latter is especially advantageous if the device 23 is configured in such a way that it can be moved or lifted manually by a user or patient, in particular using (only) one hand. In this case it is in particular conceivable that the inhaler 1 is not removed from the device 23 in order to use it, but instead the inhaler 1 is taken in combination with the device and brought to the patient's mouth for the inhalation. Preferably this can also be performed with one hand.

FIGS. 4 and 6 show the device 23 with the inhaler 1 inserted therein.

The device 23 can preferably be coupled or connected, in particular mechanically and/or electronically, to the inhaler 1, in particular so that the inhaler 1 is held by the device 23 and/or a state or tension state of the inhaler 1 or energy store 7 can be altered by means of the device 23.

The inhaler 1 can preferably be coupled (mechanically and/or electronically) to the device 23 by inserting it into or placing it on the device 23.

The coupling or insertion or placement on the inhaler 1 can be effected by an, in particular exclusively, linear and/or axial movement. The coupling or insertion or placement of the inhaler 1 is preferably executed manually or by a patient or user of the inhaler. In principle however other solutions are also conceivable here.

The device 23 preferably comprises a standing surface 24, which can be at least substantially flat or planar. In a position of use of the device 23 the standing surface 24 is arranged on the underside of the device 23, or the underside of the device 23 forms the standing surface 24.

Relative location or position details such as "below", "above" or the like refer in each case to the usual position of use of the device 23 and/or of the inhaler 1 when inserted into the device 23, in which the device 23 stands or rests with its standing surface 24 on a preferably substantially flat and/or horizontal surface, and the inhaler 1 is accordingly oriented vertically with its axis of rotation D, as is also illustrated in the figures. Thus, the terms "above", "below" or the like have the usual meaning as regards a vertical or perpendicular arrangement, as illustrated in particular in FIG. 6. "Above" is consequently preferably a side facing away from the centre of the earth, while "below" is a side facing towards the centre of the earth, preferably extending transverse or perpendicular to the gravitational force.

The device 23 preferably comprises or forms a receptacle 25 for the inhaler 1. In particular the receptacle 25 is designed for receiving or inserting the inhaler 1, or the inhaler 1 can be inserted into the receptacle 25. The receptacle 25 is accordingly shaped corresponding to the inhaler 1.

The receptacle 25 is designed in particular as a depression and/or a blind hole-shaped recess in the device 23. The receptacle 25 preferably comprises a base 25a on an axial end side. The base 25a preferably extends at least substantially parallel to the standing surface 24 and/or perpendicular to the axis of rotation D.

The receptacle 25 is preferably shaped corresponding to and/or complementary to the inhaler 1. The receptacle 25 is preferably formed at least substantially hollow-cylindrically and/or is bounded in the radial direction by an at least substantially cylindrical wall. The wall of the receptacle 25 is not shown in FIGS. 4 and 5 and is indicated only schematically in FIG. 6. The receptacle 25 or the wall delimiting the receptacle 25 can be formed in one part or several parts.

The depth of the receptacle 25, i.e. its extension parallel to the axis of rotation D, in particular measured from the base 25a to the upper edge 33, is preferably several centimetres, in particular at least 3 cm, particularly preferably at least 5 cm and/or at most 10 cm, particularly preferably at most 7 cm. This is conducive to a secure retention or secure storage of the inhaler 1 in the device 23.

Preferably the receptacle 25 has, perpendicular to the axis of rotation D, at least substantially a round, in particular oval and/or circular, cross section. The diameter of the receptacle 25 perpendicular to the axis of rotation D is preferably between 2 cm and 5 cm, preferably about 3 cm.

The inhaler 1 inserted into the receptacle 25 or its housing part 18 and/or inner part 17 can be or will be partially or completely accommodated or arranged in the receptacle 25.

The receptacle 25 is preferably arranged such that the axis of rotation D of the inhaler 1 inserted into the device 23 or receptacle 25 extends or is arranged vertically when the standing surface 24 is aligned horizontally.

The axis of rotation D of the inhaler 1 inserted into the device 23 or receptacle 25 preferably extends perpendicular to the standing surface 24. The receptacle 25 extends with its longitudinal extension preferably parallel to the axis of rotation D and/or surrounds the axis of rotation D.

The axis of rotation D of the inhaler 1 inserted into the device 23 is or preferably forms (at the same time) a central axis, longitudinal axis and/or axis of symmetry of the device 23 and/or the receptacle 25.

The inhaler 1 can be withdrawn from the device 23 or removed from the receptacle 25, in particular after an addition of energy to the energy store 7 and/or when the inhaler 1 is in a triggering-ready state. In particular the inhaler 1 can be decoupled by removing it from the device 23 or the receptacle 25. It is possible for the device 23 to be configured so that the inhaler 1 cannot be removed from the device 23 during the addition of energy or tensioning or when non-tensioned, or only by or after unlocking.

The decoupling or removal of the inhaler 1 preferably takes place by an (exclusively) linear and/or axial movement. For example, a groove guide can be provided on the inhaler 1 and the device 23, so that the inhaler 1 can be coupled to and/or decoupled from the device 23 by an (exclusively) axial movement. In particular, the inhaler 1 and the device 23 comprise mutually corresponding interlocking elements, for example grooves and chamfers. Preferably a positive coupling of the inhaler 1 to the device 23 can be realised by the groove guide. In particular, a rotation-proof coupling of at least one of the housing parts 16, 17, 18 of the inhaler 1 to the device 23 can take place in this way. This is discussed in more detail later.

In the embodiments of the device 23 shown in FIGS. 4 and 5 it is preferably envisaged that the inhaler 1 with the housing lower part or lower housing part 18 is inserted into the device 23. However, embodiments are also possible in which the inhaler 1 without the housing part 18 can be inserted or is inserted into the device 23.

In particular, in the embodiment of the inhaler 1 shown in FIGS. 1 to 6 the lower housing part 18 is not absolutely necessary for the tensioning of the energy store 7 or the spring, although a manual tensioning is greatly facilitated by the lower housing part 18.

In the described inhaler 1 the housing part 18 and the inner part 17 are preferably connected or coupled to one another in such a way that, on rotation of one of the housing parts 17, 18, the other housing part 17, 18 is rotated simultaneously and/or in the same way. The housing part 17 and the housing part 18 are thus connected or coupled to one another in a rotation-proof manner.

The device 23 preferably comprises a motor drive 26. The drive 26 is designed in particular to move two housing parts, in particular the housing parts 16 and 17 and/or the housing parts 16 and 18, of the inhaler 1 inserted into the device 23 and/or coupled to the device 23, relative to one another, in particular to turn them relative to one another.

In the following the expression "the housing parts 16, 17, 18" is to be understood as a short form for "the housing parts 16 and 17 and/or the housing parts 16 and 18". Similarly, "housing part 17, 18" is to be understood as a short form for "housing part 17 and/or housing part 18".

It is however also possible for two housing parts of the inhaler 1 to be moved by means of the device 23 other than by rotating them relative to one another, for example axially and/or linearly. Preferably, in each case energy can be added to the energy store 7 of the inhaler 1 or the spring of the inhaler 1 can be tensioned by the movement of the housing parts 16, 17, 18 relative to one another. In particular the spring is tensioned, in particular compressed, by the movement of the housing parts 16, 17, 18 relative to one another.

The inhaler 1 is preferably brought into the triggering-ready state by means of the device 23, i.e. by moving the housing parts 16, 17, 18 of the inhaler 1 inserted in the device 23 relative to one another, in particular rotating them relative to one another, whereby the spring is tensioned or compressed.

The drive 26 comprises an in particular electric motor 27 and/or a transmission or a gear mechanism 28. The motor 27 is therefore preferably designed as an electric motor or can be operated electrically. A motor-driven and/or electrical rotation of the housing parts 16, 17 relative to one another and/or addition of energy to the energy store 7 or a tensioning of the inhaler 1 preferably takes place by means of the drive 26. It is also possible for the drive 26 and/or motor 27 to be designed as a direct drive.

The motor 27 is shown only schematically in the figures. The motor 27 is preferably a servo motor and/or a DC motor, for example a 6 V DC motor. The current consumption of the motor 27 is preferably about 0.7 A.

The motor 27 can however also be an asynchronous motor, a synchronous motor, a traveling wave motor and/or a step motor.

The motor 27 can also be designed as a step motor without gear mechanism assistance, for example as a permanent magnet step motor or high-torque step motor.

The drive 26 or motor 27 can preferably be operated with a battery and/or a storage battery. This is preferably integrated in the device. This will be discussed in more detail later.

The transmission or the gear mechanism 28 is preferably designed to transmit a movement of the motor 27 to the inhaler 1 and/or to move, in particular rotate, one of the housing parts 16, 27, 18 of the inhaler 1 by means of the motor 27. In other words, the two housing parts 16, 17, 18 are moved, in particular rotated, relative to one another by in any case the movement of one of the housing parts 16, 17, 18.

The drive 26 or motor 27 is preferably designed to tension or compress the energy store 7 or the spring with a force of at least 20 N, preferably at least 30 N, and/or at most 100 N, preferably at most 80 N, particularly preferably at most 60 N. The length of the energy store 7 or the spring during the tensioning is preferably shortened by at least 2 mm, preferably at least 9 mm, and/or at most 30 mm, preferably at most 20 mm.

The work or energy to be expended in order to add energy to the storage device 7 or for a tensioning procedure is preferably more than 20 cNm and/or less than 100 cNm, preferably less than 80 cNm, particularly preferably less than 60 cNm, in particular less than 50 cNm. The device 23, in particular the drive 26 and/or motor 27, preferably provides such an energy and/or such a torque and/or performs such a work on the inhaler 1 in order to add energy to the energy store 7, in particular by or on rotation of the housing parts 16, 17, 18 relative to one another.

To transmit a movement from the motor 27 to the inhaler 1 or at least one housing part 16, 17, 18 of the inhaler 1, the gear mechanism 28 preferably comprises a gearwheel 29a, 29b or multiple gearwheels 29a, 29b, which preferably engage and/or cooperate with one another. In order to differentiate between them, the gearwheels are termed hereinafter "first" gearwheel 29a and "second" gearwheel 29b. It is also possible that the "first" gearwheel 29a is omitted, so that only one gearwheel 29a, 29b is present, which however is still referred to as "second" gearwheel 29b. In particular the term "second gearwheel" does not imply that multiple gearwheels have to be present.

Alternatively or additionally, the gear mechanism 28 can be a Maltese cross gear (not shown), an epicyclic gear, an ellipto-centric gear, a planetary gear or some other gear mechanism.

The drive 26, the motor 27 and/or the gear mechanism 28 are preferably arranged at least partially within the device 23, in particular so that they are concealed or are not visible to a user (not shown). The device 23 preferably comprises a housing for the drive 26, the motor 27 and/or the gear mechanism 28.

A torque of at least 0.2 Nm, preferably at least 0.3 Nm, in particular at least 0.4 Nm and/or at most 1.1 Nm, preferably at most 1.0 Nm, in particular at most 0.9 Nm, particularly preferably at most 0.8 Nm, can preferably be provided and/or transmitted to the inhaler 1 or a housing part of the inhaler 1 by means of the drive 26, the motor 27 and/or the gear mechanism 28.

The transmission of the torque from the drive 26, motor 27 and/or gear mechanism 28 to the inhaler 1 or a housing part of the inhaler 1 preferably takes place by means of the coupling device 30b.

The device 23 and/or the drive 26 are preferably designed to put the inhaler 1 into the triggering-ready state in at most 5 s, preferably at most 3 s, in particular at most 1 s, or to add the required energy to the energy store 7 or to tension the spring of the inhaler 1. The time for the addition of energy to the energy store 7 is particularly preferably about 0.5 s.

The device 23 preferably comprises two coupling devices 30a, 30b for coupling the inhaler 1 and/or the housing parts 16, 17, 18 of the inhaler 1 to the device 23. It is however also possible for the device 23 to have only one or more than two coupling devices 30a, 30b.

The coupling devices 30a, 30b can preferably each be coupled, in particular mechanically, to one of two housing parts 16, 17 18 of the inhaler 1, so that by means of the coupling devices 30a, 30b the two housing parts 16, 17, 18 can be moved, in particular rotated, relative to one another. In the specifically illustrated embodiment according to FIGS. 5 and 6 the coupling device 30a can be coupled to the housing part 16 and the coupling device 30b can be coupled to the housing part 18, for example.

The coupling devices 30a, 30b are preferably designed differently.

Preferably the receptacle 25 comprises or forms the coupling device 30a and/or the drive 26 comprises or forms the coupling device 30b.

The device 23 can in particular be mechanically coupled or (temporarily) connected to the inhaler 1 by means of the coupling devices 30a, 30b. In particular a positive and/or rotation-proof connection between the device 23 and the inhaler 1 or its housing parts 16, 17, 18 can be produced by means of the coupling devices 30a, 30b.

The coupling devices 30a, 30b and the inhaler 1 or their housing parts 16, 17, 18 thus preferably mesh positively with one another in such a way that a relative movement, in particular rotation, of the housing parts 16, 17, 18 is enabled and/or that the inhaler 1 can be respectively coupled and/or decoupled from the device 23 or the coupling devices 30a, 30b by a linear and/or axial movement.

The coupling devices 30a, 30b are preferably designed corresponding to the shape of the inhaler 1 or the housing parts 16, 17, 18.

The inhaler 1 or the housing part 16 and/or the housing part 17, 18 preferably comprise one or more coupling sections 31, which are designed in particular as externally and/or radially projecting elevations. This can be seen in particular in FIG. 3. The inhaler 1 particularly preferably comprises two coupling sections 31.

A coupling section 31 is preferably a part or section which is configured to add, when actuated, energy to the energy store 7 or to tension the spring. In particular there are one or more sections, via which the housing parts 16, 17, 18 can be mechanically coupled and/or moved, so that the spring can be tensioned. The coupling sections 31 are preferably formed corresponding to or complementary to the coupling device 30a, 30b, so that the inhaler 1 can be tensioned by means of the device 23.

The coupling sections 31 preferably form projections and/or undercuts in such a way as to enable a torque-proof or rotation-proof coupling to the device 23. In this way the device 23 can move, in particular rotate, the housing parts 16, 17, 18 relative to one another so that the spring is tensioned.

The coupling sections 31 are preferably arranged radially and/or diametrically opposite and/or symmetrically on the inhaler 1 or the housing part 16, the housing part 17 and/or the housing part 18.

The coupling sections 31 preferably extend axially or parallel to the axis of rotation D in the direction of their main extension and/or are preferably elongated.

Preferably the outer circumference of the inhaler 1 or corresponding housing part 16, 17, 18 in the region of the coupling sections 31 is enlarged by the coupling sections 31, or the inhaler 1 has an enlarged circumference (on account of the coupling sections 31) in the area of the coupling sections 31.

Particularly preferably the inhaler 1 or the housing part 16, 17, 18 is formed at least substantially cylindrical at least in the region of the coupling sections 31, and/or has an at least substantially circular outer circumference in this region, wherein the coupling sections 31 project outwardly from the circular or cylindrical section or form inwardly directed indentations.

The coupling section 31 can extend over the two housing parts 16, 17, 18, in particular so that when the housing part 18 is installed a continuous elevation or depression is formed in particular.

Gripping surfaces or resistance surfaces are preferably formed by the coupling sections 31, by means of which the (manual) rotation of the housing parts 16, 17, 18 relative to one another is facilitated for a user (not shown). In particular the coupling sections 31 or elevations facilitate and/or enable a relative movement, in particular rotation, of the housing parts 16, 17, 18 relative to one another.

The first coupling device 30a and/or the second coupling device 30b are preferably designed to positively engage on the coupling sections 31 or the elevations, to engage behind these and/or to engage in these, as illustrated by way of example in FIG. 6. In particular, a mechanical coupling or positive connection of the device 23 or the coupling devices 30a, 30b to the inhaler 1 or the housing parts 16, 17, 18 is effected in this way.

The first coupling device 30a is preferably formed by or comprises one or more recesses 32a.

In the illustrated example the recesses 32a are arranged on an upper and/or entry-side edge 33 of the receptacle 25. However, the recesses 32a can also extend from the edge 33 downwards into the receptacle 25, in particular parallel to the axis of rotation D.

Particularly preferably the number of recesses 32a corresponds to the number of coupling sections 31. Most particularly preferably the first coupling device 30a has two recesses 32a or the first coupling device 30a is formed by two recesses 32a.

The recesses 32a and/or the edge 33 are preferably designed or shaped corresponding to and/or complementary to the coupling section 31 or the coupling sections 31. The inhaler can thereby be coupled to the device 23, and/or in the case where the inhaler 1 is inserted in the device 23 the coupling section 31 can be held in the recesses 32a by positive engagement against a rotation about the axis of rotation D. Alternatively or additionally the inner contour of the edge 33 can accordingly correspond to the outer contour of the inhaler 1 or the housing part 16, the housing part 17 and/or the housing part 18. Preferably the housing part 16 connected or coupled to the first coupling device 30a can only be moved axially or parallel to the axis of rotation D when the inhaler 1 is inserted into or coupled to the device 23.

By means of the coupling sections 31, the first coupling device 30a and/or the recesses 32a an oriented insertion of the inhaler 1 into the device 23 is preferably effected, in particular an insertion in a defined rotational position of the inhaler 1 with respect to the axis of rotation D.

In the illustrative example shown in the figures, the inhaler 1 has elevations and the device 23 has recesses 32a assigned to the elevations. However, here a reverse arrangement is also possible, so that the inhaler 1 has recesses and the device 23 has elevations or projections that engage in the recesses of the inhaler 1. Furthermore, other solutions are also possible, in which the inhaler 1 can be positively coupled to the device 23 by inserting it in the device 23.

For example, it is possible that the first coupling device 30a is designed to engage with or take hold of gripping aids or flat portions 16a of the housing part 16. The first coupling device 30a is preferably coupled to the flat portions 16a by means of a spring clamp, wherein coupling elements (not shown) of the first coupling device 30a can be biased radially inwardly or tensioned inwardly by means of springs, so that during or after insertion of the inhaler 1 the coupling elements are pressed against the flat portions 16*a* by means of the springs and thus hold the housing part 16 in a rotation-proof manner. In particular, a positive and/or purely conclusive coupling can thus be realised.

The first coupling device 30*a* is preferably designed to hold the (upper) housing part 16 or only one of the housing parts 16, 17, 18 in a rotation-proof manner in the device 23 by means of the coupling sections 31. By inserting the inhaler 1 preferably therefore only one of the housing parts 16, 17, 18 is coupled to the coupling device 30*a* or connected to it in a positive manner. The other housing part 16, 17, 18, in particular the housing part 17 and/or the housing part 18, are preferably movable, in particular rotatable, relative to the coupling device 30*a* when the inhaler 1 is inserted into or coupled to the device 23.

The second coupling device 30*b* is preferably arranged or designed to be movable, in particular rotatable, relative to the receptacle 25 and/or relative to the first coupling device 30*a*.

The second coupling device 30*b* is preferably designed to move one of the housing parts 16, 17, 18, in particular the inner part 17 and/or the lower housing part 18, so that owing to the movement of the housing part 17, 18 the housing parts 16, 17, 18 are turned or rotated against one another or relative to one another.

The second coupling device 30*b* is preferably formed by one of the gearwheels 29*a*, 29*b* and/or is designed in one piece with one of the gearwheels 29*a*, 29*b*, in particular the first gearwheel 29*a*.

Energy can be added via the second coupling device 30*b* to the energy store 7, or the spring can be tensioned preferably by means of the drive 26. In particular the second coupling device 30*b* can be driven by means of the motor 27 and the second coupling device 30*b* is coupled to one of the housing parts 16, 17, 18 of the inhaler 1 when the inhaler 1 is inserted, in such a way that a movement of the motor 27 moves, in particular rotates, the housing parts 16, 17, 18 relative to one another in such a way that energy is added to the energy store 7 or the spring is tensioned.

The second coupling device 30*b* particularly preferably forms a gearwheel of the gear mechanism 28. In this case the second coupling device 30*b* can be formed radially on the inside for the positive engagement of the housing part 16, 17, 18 and radially on the outside with teeth to form the first gearwheel 29*a*. In other words the drive 26, in particular the gear mechanism 28, comprises a gearwheel 29*a* which can be driven by the motor 27 and/or by the second gearwheel 29*b* and on the inside comprises the second coupling device 30*b*. The second gearwheel 29*b* can be omitted, so that the drive 26 and/or motor 27 drives the first gearwheel 29*a* directly.

The second coupling device 30*b* or the first gearwheel 29*a* forming or comprising the second coupling device 30*b* is preferably arranged on the base 25*a* of the receptacle 25 formed in particular as a blind hole, and/or on a side of the receptacle 25 facing away from the edge 33. In particular the second coupling device 30*b* is arranged below the first coupling device 30*a* and/or opposite the edge 33. The second coupling device 30*b* is preferably arranged on an axial end side and/or within the receptacle 25, as indicated schematically in FIG. 6.

The second coupling device 30*b* or the first gearwheel 29*a* forming or comprising the coupling device 30*b* is preferably arranged in the device 23 or the receptacle 25 in such a way that the main extension plane of the first gearwheel 29*a* extends transversely, in particular perpendicularly, to the axis of rotation D and/or that teeth 34 of the first gearwheel 29*a* protrude radially from the first gearwheel 29*a* with respect to the axis of rotation D.

The first gearwheel 29*a* is preferably arranged symmetrically and/or in such a way relative to the axis of rotation D that the axis of rotation D also forms the axis of rotation of the first gearwheel 29*a*.

Preferably the second coupling device 30*b* or the first gearwheel 29*a* forming or comprising the second coupling device 30*b* is designed to be at least partially hollow-cylindrical and/or annular, in particular wherein the teeth 34 project radially inwardly and/or outwardly from the ring or hollow cylinder. The teeth 34 extend in the axial direction preferably only over part of the first gearwheel 29*a* or hollow cylinder or ring, so that, in particular at an upper end of the first gearwheel 29*a*, a collar-like or rim-like, preferably (hollow) cylindrical section without teeth 34 or a toothless section is formed.

Preferably the coupling device 30*b* or the first gearwheel 29*a* at least partially surrounds the inhaler 1 inserted in the device 23 or its housing part 17 and/or housing part 18. The inhaler 1 inserted in the device 23 or its housing part 17, 18 is preferably arranged at least partially radially within and/or on the inside of the coupling device 30*b*. In particular the second coupling device 30*b* includes or encloses a lower section of the inhaler 1 or housing part 17, 18 inserted into the device 23.

The second coupling device 30*b* or the toothless section preferably comprises one or more, particularly preferably two, recesses 32*b* for coupling the first gearwheel 29*a* or the second coupling device 30*b* to the coupling section 31 or the coupling sections 31.

In the illustrated exemplary embodiment the recesses 32*b* are arranged on an upper edge of the first gearwheel 29*a* or coupling device 30*b* and/or are rectangular. The recesses 32*b* preferably lie radially or diametrically opposite one another.

Figure 7:
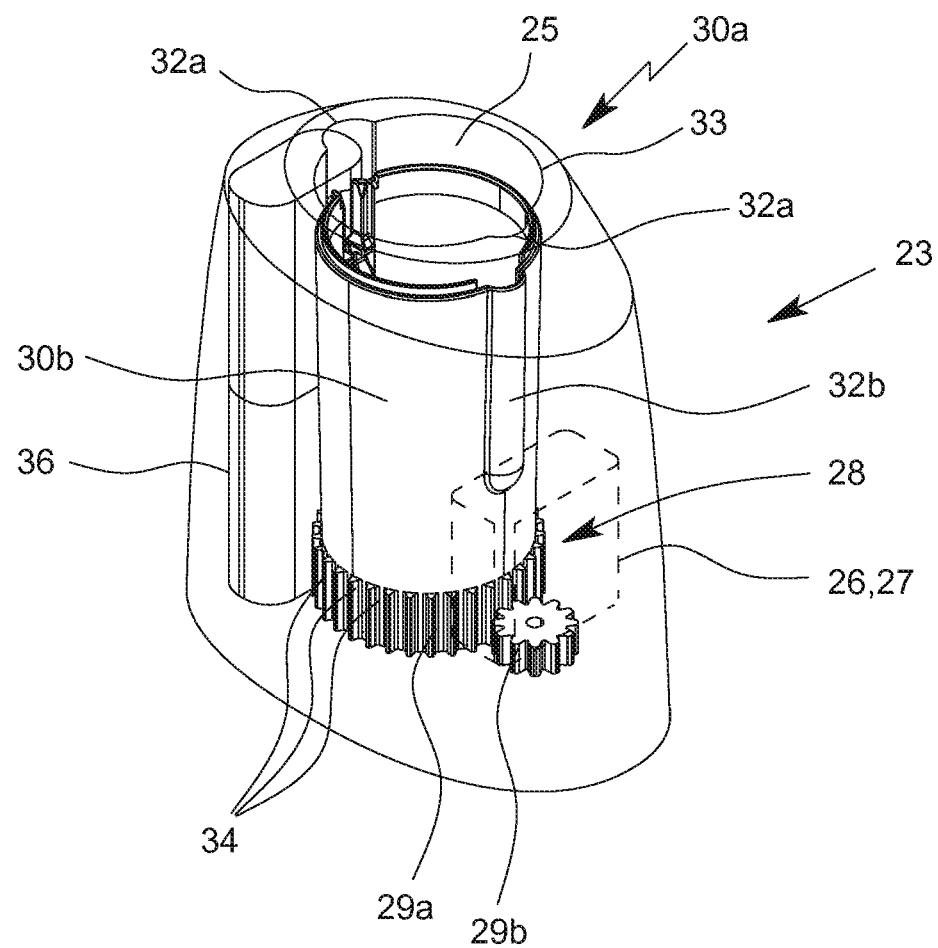
FIG. 7 is a schematic, partially transparent perspective illustration of the device according to a further embodiment.

According to a further embodiment illustrated in FIG. 7, the coupling device 30*b* is formed in the manner of a cup with a cup base and an at least substantially cylindrical side surface. This cup can be formed in one piece with the first gearwheel 29*a* and/or integrally formed on the first gearwheel 29*a* and/or can be coupled or connected in another way in a rotation-proof manner to the first gearwheel 29*a*. In the illustrated example the cup comprises teeth 34 externally on a lower axial end or section on the side surface of the cup base. As regards the cup, the recesses 32*b* are preferably formed in the side surface, in particular the toothless section, so that the coupling sections 31 engage in and/or are coupled to the recesses 32*b* in a rotation-proof manner when the inhaler 1 is inserted in the receptacle 25 or cup. In particular, the cup is designed in such a way that the housing part 17, 18 abuts at least over a large area and/or completely on the side surface of the cup or the recesses 32*b* when the inhaler 1 or the housing part 17, 18 is inserted into the cup. Preferably the first gearwheel 29*a* is arranged below or on a lower axial end of the cup if it is not formed in one piece with the cup or if the cup itself has no teeth 34. However, other solutions are also possible here.

The inhaler 1 can preferably be connected or coupled to the second coupling device 30*b*, or inserted into the latter, in particular into the recesses 32*b*, by axial and/or linear insertion or sliding, preferably wherein the coupling sections 31 on insertion or of the inserted inhaler 1 engage in the recesses 32*b* and in this way connect or couple the corresponding housing part 17, 18 in a rotation-proof manner to the second coupling device 30*b*.

The inhaler 1 (inserted into the device 23) can preferably be moved axially relative to the second coupling device 30*b*, in particular can be decoupled or removed or withdrawn from it and/or is coupled in a rotation-proof manner, in particular positively, to the second coupling device 30*b*, preferably by means of the recesses 32*b*.

The coupling device 30*a* or 30*b* can also be designed in such a way that it has no recesses. In particular it is possible for the coupling device 30*b* to grip or encompass the inhaler 1 or one of the housing parts 16, 17, 18, and/or to engage in one of the housing parts 16, 17, 18.

In general it is envisaged that the coupling device 30*a*, 30*b* can be connected positively and/or frictionally in a rotation-proof manner to the inhaler or one of the housing parts 16, 17, 18.

Preferably an axial end position for the inhaler 1 is defined by the second coupling device 30*b* and/or recesses 32*b*. The inhaler 1 can be moved, in particular slid in or installed on the receptacle 25 or the device 23, in particular on account of the coupling sections 31, therefore preferably not further than the end position defined by the recesses 32*b*.

The downward movement of the inhaler 1 or movement in the direction of the base 25*a* of the receptacle 25 is thus preferably restricted by the recesses 32*b* and/or the coupling sections 31. This enables a simple and defined insertion of the inhaler 1 into the device 23.

The receptacle 25 is preferably designed to hold the inhaler 1 and/or at least one of the housing parts 16, 17, 18.

Preferably when and/or by inserting the inhaler 1 into the receptacle 25 or the device 23, the drive 26 is connected to one of the housing parts 16, 17, 18, in particular the inner part 17 and/or the lower housing part 18, and the other housing parts 16, 17, 18, in particular the (upper) housing part 16, is connected to the receptacle 25, in particular the coupling device 30*a* or the recesses 32*a*. The drive 26 is connected to one of the housing parts 16, 17, 18 preferably by means of the second coupling device 30*b* and/or the recesses 32*b*.

Preferably the aforementioned connections are designed such that the housing part 16, 17, 18 connected (in a rotation-proof manner) to the drive 26 is movable, in particular rotatable, relative to the other housing part 16, 17, 18 and the other housing part 16, 17, 18 is held immovably, preferably in a rotation-proof manner, in the receptacle 25 or the first coupling device 30*a* during the tensioning.

To add energy to the energy store 7 or to put the inhaler 1 in the triggering-ready state, preferably one of the gearwheels 29*a*, 29*b* is driven, in particular caused to rotate, by means of the drive 26 or motor 27. The second gearwheel 29*b* driven by the drive 26 or motor 27 preferably engages in the coupling device 30*b* or the first gearwheel 29*a* engages with the coupling device 30*b* and/or meshes therewith, so that the coupling device 30*b* is rotated or caused to rotate about the axis of rotation D. When the inhaler 1 is inserted into the device 23, the housing part 17 and/or the housing part 18 are thus rotated relative to the housing part 16, whereby the spring is tensioned and the inhaler 1 is thereby put into the triggering-ready state.

In principle it is also possible that more than two gearwheels 29*a*, 29*b* are used or that the drive 26 or motor 27 directly drives or rotates the coupling device 30*b*. In this case the coupling device 30*b* can also be formed without the first gearwheel 29*a*, for example if a part of the drive 26 or motor 27 can be or is connected directly in a rotation-proof manner to the coupling device 30*b*.

In an alternative arrangement, not illustrated, the drive 26 comprises a worm. The worm can be driven directly by the motor shaft of the motor 27. The worm preferably engages directly in a complementary tooth system formed on the outer radial circumference of the second coupling device 30*a*. In this way a relatively high gear reduction can be generated with simple means, which facilitates the provision of the necessary torque.

Basically however there are also drive concepts different from the above.

The second coupling device 30*b* is generally preferably movable, in particular rotatable, by means of the drive 26 or motor 27 via the gear mechanism 28.

The device 23 and/or the drive 26 are preferably designed to rotate the housing parts 16, 17, 18 relative to one another, in particular by more than 90° and/or by at most 360°, in particular by at least substantially 180°.

Particularly preferably the inhaler 1 is tensioned or energy is added to the energy store 7 or the inhaler is put in the triggering-ready state by a rotation of the housing parts 16, 17, 18 relative to one another by 180° or by half a rotation of the inner part 17 and/or lower housing part 18 relative to housing part 16.

Accordingly the device 23 and/or the drive 26 are preferably designed so as to rotate the housing parts 16, 17, 18 relative one another by 180°. It is however also possible for a tensioning of the inhaler 1 or addition of energy to the energy store 7 to be effected by means of a rotation by a different angle, for example 90° or 360°. However, a complete rotation is preferably not required to put the inhaler in the triggering-ready state or to tension the spring.

In particular the inhaler 1 and/or the device 23 can be designed in such a way that the housing parts 16, 17, 18 can be rotated relative to one another only by at most 180° in an uninterrupted rotation procedure, or that a rotation by more than 180° in a single, uninterrupted movement is blocked.

The device 23 and/or the drive 26 are preferably designed to rotate the housing parts 16, 17, 18 relative to one another by a fixed (integer) partial angle of 360°, preferably in which the value of the angle is an (integral) divisor of 360. The fixed partial angle can therefore be for example 180°, 120°, 90°, 60°, 45° or 30°. Other partial angles are however also possible.

The device 23 preferably comprises one or more sensors 35 for detecting the insertion, coupling and/or state or tension state of the inhaler 1. The sensor 35 is shown only schematically in the figures.

Preferably by means of the sensor 35 it can be determined whether the inhaler 1 has been inserted completely and/or correctly into the device 23, in particular so that the inhaler 1 is coupled to the coupling devices 30*a*, 30*b* and/or an addition of energy to the energy store 7 is enabled, in particular by rotating the housing parts 16, 17, 18 relative to one another.

The sensor 35 is preferably assigned to the receptacle 25, the coupling device 30*a* and/or the coupling device 30*b*. The sensor 35 is preferably designed to detect an insertion of the inhaler 1 into the receptacle 25 and/or a coupling of the inhaler 1 or housing part 16, 17, 18 of the inhaler 1 to one of the coupling devices 30*a*, 30*b* or both coupling devices 30*a*, 30*b*. The sensor 35 is particularly preferably designed to detect the positioning of the inhaler 1 in a position of use, in which the inhaler 1 can be tensioned by means of the device 23 or energy can be added to the energy store 7. This position is especially characterised in that the coupling devices 30*a*, 30*b* are connected to the housing parts 16, 17, 18 in such a way that the drive 26 can move these, in particular rotate them, relative to one another. The inhaler 1 can thereby be tensioned. In this position the inhaler 1 is preferably fully inserted into the device 23 and/or in this position the coupling sections 31 are fully inserted into the recesses 32b.

In order to detect the insertion and/or coupling of the inhaler 1 the sensor 35 can in particular comprise or be formed by a (micro) switch or push button, which preferably can be actuated automatically or is actuated by inserting the inhaler 1. In this case it is preferred that the sensor 35 is arranged on the underside or on the base 25a of the receptacle 25, in particular so that the switch or push button comes into contact with the inhaler 1 on insertion of the latter inserted and is thereby actuated. An alternative or additional arrangement of the sensor 35 on the side is however also possible.

The sensor 35 is preferably designed to detect a correct insertion and/or coupling of the inhaler 1. In particular it can be detected by means of the sensor 35 whether the inhaler 1 has been inserted into the device 23 in such a way that the housing parts 16, 17, 18 can rotate relative to one another and/or energy can be added to the energy store 7.

The device 23 can also comprise a (further) sensor 35, with which alternatively or additionally the state or tension state of the inhaler 1 can be detected. In particular, if an insertion of the inhaler 1 into the device 23 without the housing part 18 is envisaged and/or if the lower housing part 18 is transparent, the state or tension state of the inhaler 1 can be detected via the axial position of the container 3, since the state or tension state is preferably correlated with this position, as described in more detail above.

A detection of the state or tension state can then be performed optically, for example via a reflection and/or distance measurement. It is also possible that the (further) sensor 35 is designed as a switch or push button, which is preferably arranged on the base of the receptacle 35. By means of such a sensor 35, on insertion of the inhaler 1 without a lower housing part 18 the switch or push button is or is not actuated depending on the state or tension state or on the axial position of the container 3, so that the state or tension state can be detected or determined. In this case the device 23 preferably comprises two sensors 35, so that (in addition) the insertion of the inhaler 1 can be detected independently of its state or tension state. This is particularly necessary if the inhaler 1 is on insertion into the device 23 in a state or tension state, in which the container 3 is in an axial position, in which on insertion no actuation of the switch or push button for detecting the state or tension state takes place.

However, other and/or multiple sensors 35 are also conceivable, which for example capacitively, inductively and/or optically detect the insertion and/or coupling and/or the state or tension state of the inhaler 1. In principle a determination of the state or tension state of the inhaler 1 and/or a determination of the position of the container 3 is therefore also possible if the inhaler 1 with the preferably transparent housing part 18 is or is to be inserted into the device.

In order to detect the state or tension state of the inhaler 1 or the energy store 7, the sensor 35 can be designed in particular as an optical sensor or for optical detection. As already explained above, the state or tension state of the energy store 7 correlates with an axial position of the container 3 or the axial position of the container 3 can (clearly) indicate the state or tension state of the energy store 7. Thus, via a detection of the presence of the container 3 and/or the position, in particular axial position, of the container 3 by means of the sensor 35, a detection of the state or tension state of the energy store 7 or inhaler 1 is possible.

In particular the sensor 35 can be designed to detect, record and/or determine the presence of the container 3 and/or the position or axial position of the container 3 by means of a reflection measurement of light reflected at the container base 21. Alternatively or additionally, the sensor 35 can detect the position of the inhaler 1, the container 3 and/or the state or tension state capacitively, inductively, or by detecting a contact or a pressure optically in the aforedescribed way or some other way.

Figure 8:
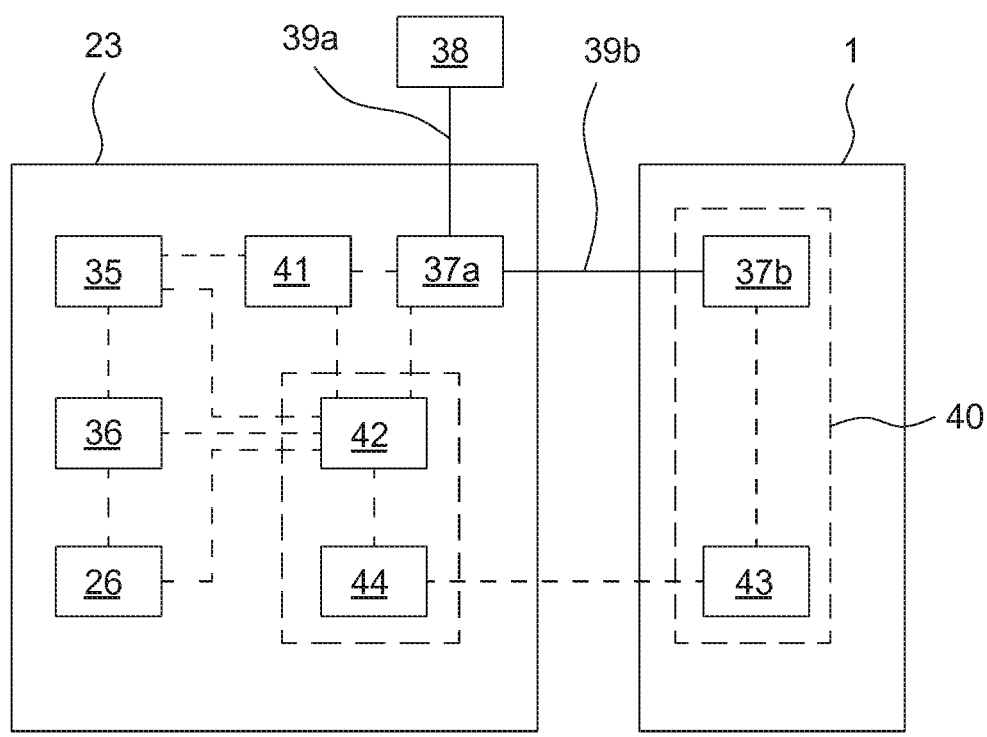
FIG. 8 is a simplified block diagram schematic illustration of the device and the inhaler according to FIGS. 4 and 6.

FIG. 8 demonstrates with the aid of a schematic block diagram a system formed by the inhaler 1 and the device 23. Here dashed lines indicate in particular electrical and/or data connections between different components or devices.

The device 23 preferably comprises a controller 36. The controller 36 is preferably designed to detect with the sensor 35 the insertion and/or coupling of the inhaler 1, preferably wherein the controller 36 and the sensor 35 are connected to one another electrically and/or in terms of information technology, as indicated in FIG. 8. The controller 36 is preferably also designed to detect the state or tension state of the inhaler 1 with the sensor 35 or in some other way or with another sensor.

Particularly preferably the controller 36 is designed to control the drive 26 or motor 27 depending on the state or tension state, preferably so that the inhaler 1 is automatically put in the triggering-ready or tensioned state by adding energy to the energy store 7. The controller 36 is preferably connected to the drive 26 electrically and/or in terms of information technology, as indicated in FIG. 8.

The controller 36 is preferably designed to limit the torque of the drive 26 or motor 27. Damage to the inhaler 1 and/or the device 23, in particular the drive 26 or motor 27 itself, can thus be avoided.

The torque applied by the drive 26 or motor 27 is preferably limited by the controller 36 to a maximum value of 0.5 Nm to 0.8 Nm. This provides in a simple way protection against an "over-turning" of the inhaler 1 and/or damage resulting therefrom. In particular the inhaler 1 comprises a locking tension mechanism that is preferably designed as described in WO 97/20590. This locking tension mechanism is intended to prevent the housing parts 16, 17, 18 being rotated relative to one another in a rotational movement by more than 180°. This locking effected by the locking tension mechanism can however be overcome by applying excessive force, which however results in the locking tension mechanism becoming worn out or damaged. Such wear or damage can be prevented by limiting the torque applied by the drive 26 or motor 27.

In the case of a drive 26 or motor 27 designed as an electric motor the torque can be limited by restricting or interrupting the power supply to the drive 26 or motor 27. In particular the controller 36 is therefore also designed to determine, in particular to measure, the power supply or the current consumption of the drive 26 or motor 27, and, depending on this, to control or regulate, in particular limit or interrupt, the drive 26 or the motor 27 or the power supply.

In other words, the device 23, the controller 36 and/or the drive 26 is thus preferably designed to stop, abort and/or interrupt a tensioning process or an addition of energy to the energy store 7, in particular to stop or switch off the drive 26 or motor 27, when a defined or predetermined maximum torque or a defined or predetermined maximum work is achieved. The maximum torque or the maximum work is preferably 0.5 Nm, 0.6 Nm or 0.8 Nm. Preferably the housing parts 16, 17, 18 are rotated relative to one another by means of the device 23 only using torques that are smaller than the maximum torque.

The controller 36 preferably comprises a control chip, in particular a microcontroller or an ASIC. The control chip preferably has an input interface for control devices such as sensors, in particular the sensor 35, and/or an output interface, in particular for controlling the drive 26.

The controller 36 is preferably designed to add energy as required to the energy store 7.

In particular the controller 36 is designed to recognise the state or tension state of the energy store 7 by means of the sensor 35, or to recognise whether it is possible or necessary to add energy to the energy store 7. In particular the drive 26 is switched on or operated or controlled by the controller 36 only when the inhaler 1 inserted into the device 23 is in the non-tensioned or non-triggering-ready state, i.e. when a use or triggering of the inhaler 1 first of all has to be prepared for by adding energy to the energy store 7 in the triggering-ready state. In this way an unnecessary tensioning and/or associated or consequential damage to the inhaler 1 and/or the device 23 are avoided.

It is however also possible that the addition of energy to the energy store 7 does not take place automatically (on insertion), and/or—alternatively or additionally—can be controlled or implemented manually by a user (not shown), for example by actuating a corresponding push button or switch (not illustrated in FIGS. 3 to 6) on the device 23, wherein the actuation of the push button or switch effects or produces an addition of energy to the energy store 7 by means of the drive 26. The triggering of the tensioning process also takes place in this connection preferably depending on the detected state or tension state of the inhaler 1. The controller 36 is in this connection preferably designed to start, during activation, the tensioning process, thus in particular the drive 26, for example by a triggering device such as a push button or switch, only when the inhaler 1 is in its non-tensioned or non-triggering-ready state. Alternatively or additionally the activation of the drive 26 is blocked by the controller 36 when the inhaler 1 is already in its triggering-ready state or energy has already been added to the energy store 7 or the spring is already tensioned.

Preferably the device 23 can be operated in a sleep mode (standby state) with little or minimum energy consumption. Particularly preferably the controller 36 comprises an activation circuit for activating the device 23 from the sleep mode.

The controller 36 is preferably designed so that the sleep mode is automatically activated after an addition of energy to the energy store 7 and/or the device 23 is activated from the sleep mode on addition of energy to the energy store 7. In particular this activation is effected by detecting an insertion of the inhaler 1 or by actuating the push button for the addition of energy to the energy store 7.

The device 23 preferably comprises a communication device 37a. The communication device 37a of the device 23 can if necessary be designed in several parts. In particular the device 23 is designed by means of the communication device 37a as a docking station (for the inhaler 1).

The inhaler 1 preferably comprises a communication device 37b. The communication device 37b of the inhaler 1 can be arranged in the lower housing part 18, in particular on the base of the housing part 18, as schematically indicated in FIG. 3.

The communication device 37a of the device 23 is preferably designed for preferably wireless communication with an external system 38 and/or with the inhaler 1 or its communication device 37b. In particular, in the case of a multi-part configured communication device 37a of the device 23 one part can be configured for communication with the external system 38 and another part for communication with the inhaler 1 or its communication device 37b.

A wired or preferably wireless data connection 39a can preferably be (temporarily) established between the communication device 37a of the device 23 and the external system 38. A wired or preferably wireless data connection 39b can preferably be (temporarily) established between the communication device 37a of the device 23 and the communication device 37b of the inhaler 1. The data connections 39a and 39b are indicated schematically in FIG. 8.

The communication device 37a of the device 23 and/or the communication device 37b of the inhaler 1 are preferably designed to send and/or receive information on the state of the inhaler 1 and/or its use. This information can include for example the state or tension state of the inhaler 1, in particular when inserted in the device 23, the number of uses or triggering operations of the inhaler 1, the amount of fluid 2 already used and/or still contained in the container 3, a counter reading of the inhaler 1, and/or a charging state of the inhaler 1. Furthermore, this information can be or include times of and/or time intervals between tensioning processes, and uses and/or triggering operations of the inhaler 1.

The external system 38 can for example be a computer, in particular in the form of a PC or server, or a portable device such as a smartphone, tablet or laptop. The external system 38 can however also be a network, such as the Internet, so that the information on the state of the inhaler 1 can be transmitted via this network directly to a doctor or other medical carer of the user of the inhaler 1.

In this way the device 23 can be designed as a compliance interface (i.e. in particular an interface for checking compliance with protocols) and/or for patient monitoring, patient supervision, dose monitoring and/or treatment monitoring. The uses of the inhaler 1 can in particular be recorded, stored, tracked and/or checked in this way, so that in particular a patient treatment compliance during a (prescribed) use of the inhaler 1 can be followed or checked. In this way dosing support can be implemented, for example by issuing advice or reminders, in particular via the device 23.

A data exchange between the communication device 37a, 37b of the inhaler 1 and/or the device 23 and the external system 38 can take place for example via WLAN, WPAN, Bluetooth, infrared, NFC, RFID and/or other suitable methods or standards. Information transmission or communication via a wired data connection 39a is however also possible.

Preferably the communication between the communication devices 37a and 37b of the inhaler 1 and the device 23 takes place via WLAN, WPAN, Bluetooth, infrared, NFC, RFID and/or other suitable method and/or other suitable standard. However, it is also possible for the communication between the communication devices 37a and 37b to take place via a wired data connection 39b, in particular if the inhaler 1 is inserted into and/or coupled to the device 23.

A data transmission or communication between the communication devices 37a, 37b of the inhaler 1 or the device 23 and/or between the communication device 37a of the device 23 and the external system 38 preferably takes place (automatically) after insertion of the inhaler 1 into the device 23 and/or only when the inhaler 1 is inserted into or coupled to the device 23.

In particular, a communication takes place only when an insertion or coupling of the inhaler 1 to the device 23 has been detected by the controller 36 and/or the sensor 35. However, it is (also) possible for a communication to take place at other times, in particular even when the inhaler 1 is not coupled to or inserted into the device 23, and/or for a continuous or uninterrupted communication to take place.

It is also possible that the inhaler 1 comprises a monitoring device, in particular a monitoring device in the form of the "monitoring device" described in WO 2011/157561 A1. In particular the communication device 30*a* can in this case be designed for communication with the interface described there, or the interface forms the communication device 37*b* of the inhaler 1. Preferably, the data stored by the monitoring device or recorded by means of the monitoring device can be transmitted to the device 23 or exchanged with the device 23. In other words, the device 23 can preferably be designed to read out the data in the monitoring device. In this connection it is preferably also possible to determine how much time has elapsed between a tensioning of the inhaler 1 by the device 23 and a use of the inhaler 1, determined in particular with the monitoring device.

The inhaler 1 and/or the device 23 can include a counter 40 for counting uses of the inhaler 1.

The counter 40 is preferably designed for the recording, detection and/or storage of uses of the inhaler 1, in particular tensioning processes implemented as or by the recording, detection and/or storage of tensioning processes executed by the device 23. In particular, doses of the substance or the fluid 2 to be atomised, which have already been dispensed by a container 3 and/or are still contained in a container 3, can be recorded and/or counted by means of the counter 40. The counter 40 can be designed for example like the monitoring device described in WO 2005/080001. However, other solutions are also possible here.

The counter 40 can be a mechanical counter or comprise a mechanical counting device, for example in the form of the spindle counter described in WO 2004/024340 A1 and also indicated in FIG. 1, or in the form of one or more counter rings with numbers affixed or applied thereto to display a counter reading or counter value.

In the case of such a mechanical counter 40 the device 23 can in particular be designed to detect, read out, scan and/or determine the counter 40 or counter reading or counter value. This can be performed for example via an optical detection of a display element or the position of a display element, in particular by a reflection measurement, distance measurement, laser triangulation and/or other optical acquisition, for example by means of a camera.

However, the counter 40 is preferably an electronic or electromechanical counter.

The counter 40 can be fixedly integrated in the inhaler 1 and/or a housing part 16, 17, 18 of the inhaler 1 and/or can be designed to be removable from the inhaler 1.

It is however also possible for the device 23 to include the counter 40.

In an arrangement of the counter 40 on or in the device 23, an insertion of the inhaler 1 into the device 23, a removal of the inhaler 1 from the device 23 and/or a changed state or tension state of the inhaler 1 between a removal and a subsequent reinsertion of the inhaler 1 can for example be determined or counted as actuation or use of the inhaler 1.

It is also possible for a counter 40 arranged on or in the device 23 to include a detection device to detect an indicator of the inhaler 1 for displaying a counter reading or counter value or a position of such an indicator. Such an indicator can for example be a movable element whose position is altered with each actuation or use of the inhaler 1, for example an axially displaceable indicator element or also a counting ring that is rotated further with each actuation or use of the inhaler 1. However, other solutions are also conceivable here.

The counter 40 preferably comprises a reset device for resetting the counter. The reset device is preferably designed to change, in particular reset, delete and/or to set or change to "0" a displayed and/or stored counter value or counter reading. The resetting of the counter 40 can be effected mechanically, electronically and/or electromechanically.

A "counter value" and/or "counter reading" should be understood in particular as a value or a number that corresponds to the number of uses of the inhaler 1 (detected by the counter 40), in particular after a resetting of the counter 40. Even if therefore all uses of the inhaler 1 are or can be recorded with the counter 40, the counter value or counter reading then however preferably corresponds only to the number of uses after the last resetting of the counter 40. In particular the terms "counter value" and "counter reading" should be understood synonymously within the meaning of the present invention.

The counter 40 preferably comprises an actuating element. The actuating element is preferably designed and/or arranged so that the counter 40 can be reset by actuating the actuating element. The reset device preferably comprises the actuating element.

The actuating element can be designed as a key, push button, switch and/or actuating field, which can be actuated manually, in particular pressed, by a user (not shown).

The actuating element is preferably coupled and/or connected to the reset device, preferably so that the reset device is controlled or operated or can be controlled or operated by actuating the actuating element. Particularly preferably an actuation of the actuating element effects a resetting of the counter 40 by means of the reset device.

The counter 40 can be designed to determine a number of uses of the inhaler 1 that have occurred within a predefined or predefinable time window.

The counter 40 preferably comprises a treatment plan or a usage protocol. Hereinafter the terms "treatment plan" and "usage protocol" are to be understood synonymously, and therefore mean the same in the context of the present invention.

A usage protocol is a protocol that specifies how the inhaler is to be used by the user or patient. In particular, a usage protocol specifies at what times, at what time intervals, how often and/or at what frequency, in particular within a certain time window such as a day, a patient or user should use the inhaler or should inhale a medicament by using the inhaler.

For example, a usage protocol can be or include the instruction to take or inhale a medication with the inhaler three times a day, especially at specified times or times, or to inhale two doses four times a day. Preferably an optimal treatment or therapy is achieved or ensured by following the treatment plan or the use protocol.

In particular, an instruction "to be used" in the meaning of the present invention is understood to mean a (not yet accomplished) use according to the usage protocol and/or a use that should or is intended to be observed (in the future) according to the usage protocol.

The counter 40 preferably comprises the communication device 37*b* and/or the counter 40 can be connected to the communication device 37*b* for data transmission and/or via a data connection to the communication device 37*b* and/or the communication device 37*a*, as indicated in FIG. 8. Consequently the counter 40, if it is provided in the inhaler 1, can transmit counter information to the device 23 via the communication devices 37b, 37a. The device 23 can in turn store, forward and/or evaluate the counter information. In this connection the device 23 can output information or a signal on the basis of the counter information, in particular as regards a pending and/or incorrect use and/or as regards a status of the inhaler 1, for example regarding doses or the like still available in the container 3.

Preferably the inhaler 1 or its communication device 37b is designed for the exclusive communication with the device 23 or its communication device 37a and/or the inhaler 1 or its communication device 37b does not communicate directly with the external system 38, but only indirectly via the communication device 37a of the inhaler 1 and/or the data connections 39a and 39b. The device 23 is in this regard a type of firewall or gateway. The device 23 comprises in this case a data connection 39b to the inhaler 1 and inhaler-related information such as a counter reading is transmitted externally and/or made available for retrieval only via the device 23. Other solutions are however also possible here.

In particular, information on uses that have been completed and/or are to be carried out (within the time window) can be sent and/or received with the communication device 37b of the device 23.

The information on the uses that have been completed and/or are to be carried out (within the time window) can preferably be transmitted to the communication device 37a of the inhaler 1 or to the device 23 and/or via the data connection 39b.

The transmitted or transmissible information can include or relate to the following (non-exhaustive list): number of uses completed within the time window and/or uses to be carried out within the time window, times of uses, time intervals between uses and/or triggering of the inhaler 1, usage protocol, result of a comparison of the usage protocol with detected or counted or completed uses, counter reading, counter value.

Preferably the device 23 or controller 36 is designed to control the drive 26 or an addition of energy or a tensioning process depending on a counter value and/or the information transmitted by the counter 40, in particular depending on the result of a comparison of the usage protocol with completed uses. If necessary it is also possible that the energy store 7 or the spring is not (initially) tensioned after an insertion of the inhaler 1, for example in order to prevent an overdosing and/or a premature use or use deviating from the use protocol, and/or that energy is not added to the energy store immediately after the insertion, but only at a later point in time.

The device 23 preferably comprises an in particular electronically operated output device 41, which is designed for the preferably optical and/or acoustic output of information on the state of the inhaler 1 and/or its use(s).

Preferably the output device 41 is electrically and/or data-technically connected to the controller 36 and/or the sensor 35 and/or can be controlled or is controlled by the controller 36, in particular on the basis of signals that are transmitted from the sensor 35 to the controller 36 or are transmitted to the controller 36. In particular the control takes place based on or taking into account the detected state or tension state of the inhaler 1 and/or the counter reading.

The output device 41 can comprise a display and/or a loudspeaker and/or a lamp and/or a vibration alarm, or are formed by these. The output device 41 is indicated only schematically in the figures.

Preferably information that can be sent and/or received with the communication device 37a can be output with the output device 41, or corresponding signals can be output with the output device 41.

The output device 41 or the display can be for example an LCD screen, an LED screen or an OLED screen.

Alternatively or additionally the output device 41 can be formed by or comprise one or more light sources, for example in the form of LEDs.

Preferably the output device 41 is designed to show or optically display information on the state or tension state of the inhaler 1 and/or the device 23, a charging level of the inhaler 1, and/or information on the doses of the fluid 2 that have already been dispensed and/or are still available or dispensable. This can be implemented for example by the display of information texts, display of corresponding (abstract) symbols or graphics, display of corresponding numbers and/or via a colour display.

A user, not shown, can preferably be informed of the state, in particular the tension state, of the inhaler 1 by means of the information output or displayed by the output device 41, so that a correct use is ensured and/or the user is informed of any malfunctions.

Warnings and/or instructions can be issued by means of the output device 41, for example if medication is not taken using the inhaler 1 in accordance with instructions or according to a treatment plan, the inhaler 1 is loaded, and/or the container 3 needs to be replaced. This is particularly conducive to an improved patient compliance.

The output device 41 can also be connected (at least indirectly) to the sensor 35 or be in contact therewith. In particular it is possible for the output device 41 to indicate whether the inhaler 1 is or has been inserted completely or correctly into the device 23. It is possible that a user, not shown, may be requested by means of a text displayed by the output device 41 to insert the inhaler 1 completely and/or correctly once more into the device 23.

Furthermore, it is possible for the output device 41 to indicate whether the inhaler 1 is blocked for a further actuation or use (for example by the blocking device described in more detail above), if the container 3 is present or not present or the like.

Corresponding signals, warnings and/or instructions can obviously be output optically and also, alternatively or additionally, acoustically.

Corresponding information and/or warning signals can preferably be output optically and, alternatively or additionally, via the (optional) loudspeaker. This can be accomplished for example by means of simple acoustic signals such as a beep or special tone sequences and/or by the acoustic output of complete sentences in human speech.

The device 23 preferably comprises an energy supply device 42 for supplying the device 23, especially the drive 26, with electrical energy in particular. The device 23 can be operated electrically by means of the energy supply device 42.

The energy supply device 42 can for example be formed by a power connection and/or a mains cable or can comprise this. Alternatively or additionally, the energy supply device 42 can have or can be formed by a battery, a storage battery and/or another energy store. The energy supply device 42 can preferably be connected to a power network and can thereby be charged. In particular the energy store of the energy supply device 42 can be charged by connecting it to a power grid.

The energy supply device 42 is preferably designed to supply the drive 26, the motor 27, the sensor 35, the controller 36, the communication device 37a and/or the output device 41 with (electrical) energy or current, as schematically indicated in FIG. 8. Particularly preferably the energy required for the addition of energy to the energy store 7 or inhaler 1 is provided by means of the energy supply device 42.

By means of the energy store of the device 23, the drive 26, a display and/or other electrically operable devices can for example be operated or supplied with electrical energy.

The energy store of the device 23 is preferably a nickel-cadmium storage battery, a nickel-metal hydride storage battery, lithium-ion storage battery, or a lithium-polymer storage battery. The energy store is preferably rechargeable. However, other solutions are also possible here.

The energy store can also be a combination storage device consisting of a storage battery or a battery in combination with a high-capacity capacitor. This combination has the advantage that high discharge currents can as a rule be drawn from a high-capacity capacitor, since it has a low internal resistance. Preferably the high-capacity capacitor is an electronic double-layer capacitor (EDLC).

Preferably the amount of energy stored or storable in the energy store of the device 23 is preferably sufficient to carry out at least 60, preferably at least 120, in particular at least 180, particularly preferably at least 240 tensioning operations of the energy store 7 or the spring by means of the drive 26. A tensioning process is in particular in this connection a complete tensioning of the spring or a conversion of the inhaler 1 from the non-tensioned (non-triggering-ready) state to the tensioned (triggering-ready) state. In this way a user or patient can use the device 23 for several days or weeks, in particular at least 3, 4 or 5 weeks, to tension the inhaler 1 before a recharging or renewal of the energy store 34 is necessary.

The energy store of the device 23 preferably has a capacity of at least 800 mAh, preferably at least 1,000 mAh, in particular at least 1,500 mAh, particularly preferably at least 2,000 mAh, in particular at 3.6 V, 7.2 V or 10.8 V nominal voltage.

The device 23 preferably comprises a charging device 44 and/or a connector for charging an (electrical) energy store 43 of the inhaler 1. Thus, the device 23 is preferably designed as a charger and/or charging station for the inhaler 1. An "electrical" energy store 43 is understood here to mean an energy store 43 by means of which electrical energy can be stored and/or released, even if the storage itself takes place chemically for example. In particular, the (electrical) energy store 43 should not be confused with the (mechanical) energy store 7, which in the illustrative example is designed as a spring.

By means of the energy store 43 of the inhaler 1, counters 40 and/or other electrically operable devices of the inhaler 1 can for example be operated and supplied with electrical energy.

The energy store 43 of the inhaler 1 is preferably a nickel-cadmium storage battery, a nickel-metal hydride storage battery, lithium-ion storage battery, or a lithium-polymer storage battery. The energy store 43 is preferably rechargeable. Other solutions are however also possible here.

Preferably the energy store 43 of the inhaler 1 is charged, in particular automatically, when the inhaler 1 uses the device 23 or is coupled to it, and/or after an insertion or coupling of the inhaler 1—as described above—has been detected.

The energy store 43 of the inhaler 1 can be designed to operate one or more sensors and/or counters 40 of the inhaler 1. Furthermore, alternatively or additionally it is preferred that the energy store 43 of the inhaler 1 supplies the communication device 37b of the inhaler 1 with energy. In this way the inhaler 1 can transmit information to the device 23 by means of the communication device 37b, in particular concerning the use, the counter reading and/or doses remaining in the container 3.

The energy store 43 of the inhaler 1 can be relatively small, and for example be designed to operate only the counter 40. The energy for establishing the data connection 39a between the inhaler 1 and the device 23 can be transferred directly from the device 23 to the inhaler 1 during normal operation when the inhaler 1 is inserted into the device 23.

The coupling between the inhaler 1 and the device 23 for the purpose of supplying the inhaler 1 with energy or for charging the energy store 43 by means of the charging device 44 can be implemented by galvanic contact, in particular spring contacts and/or inductively. In the latter case both the inhaler 1 and the device 23 have mutually corresponding induction coils for transferring electrical energy from the device 23 to the inhaler 1.

The energy supply device 42 preferably comprises the charging device 44 and/or the energy supply device 42 is electrically connected and/or can be connected to the charging device 44. The charging device 44 can however also be realised independently of the energy supply device 42.

Figure 9:
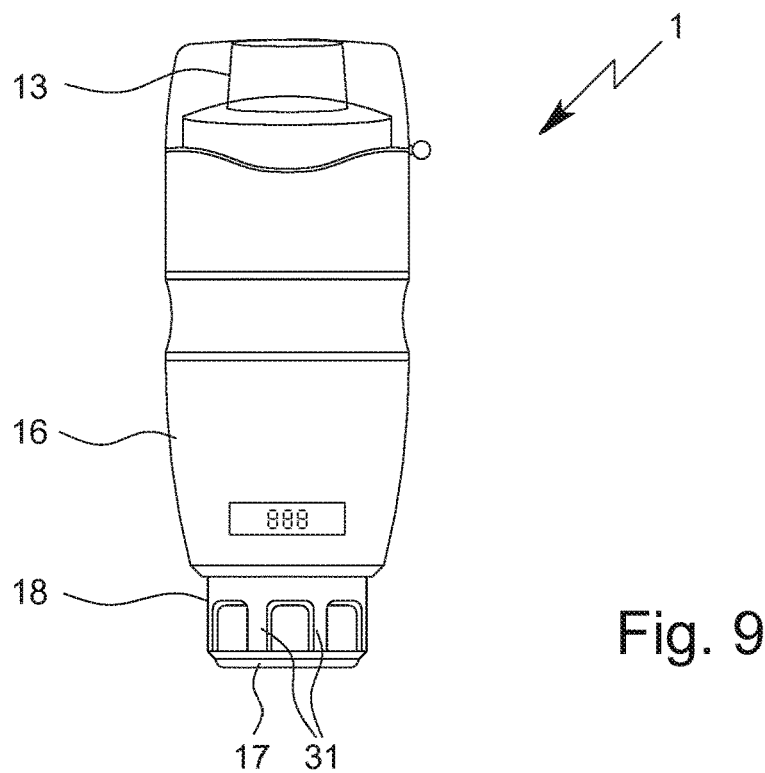
FIG. 9 is a front view of an inhaler according to a further embodiment.
Figure 10:
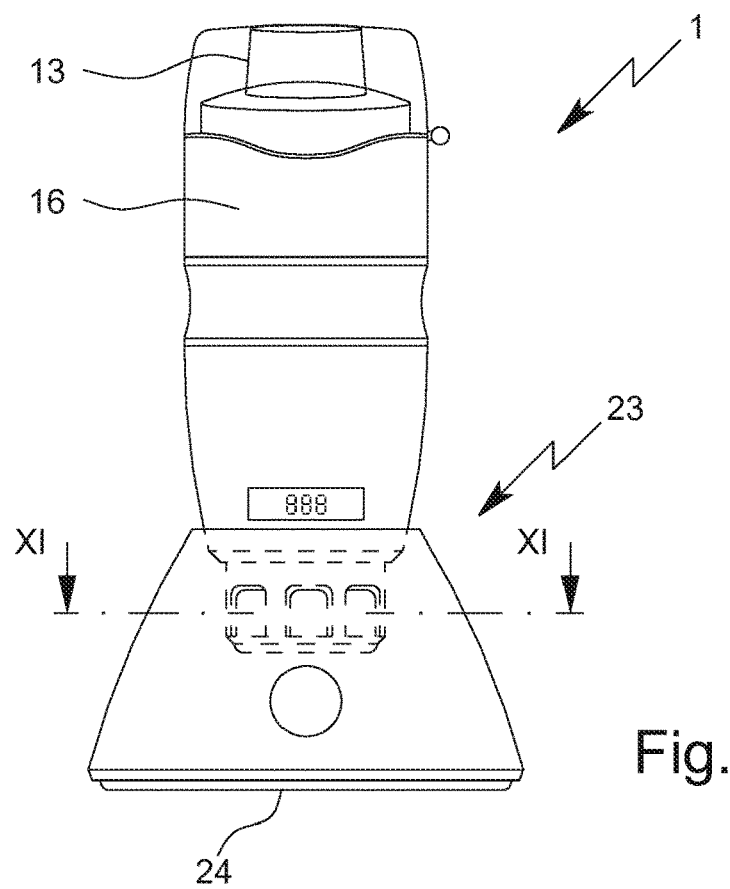
FIG. 10 is a front view of a proposed device according to a further embodiment with inserted inhaler according to the embodiment of FIG. 9.
Figure 11:
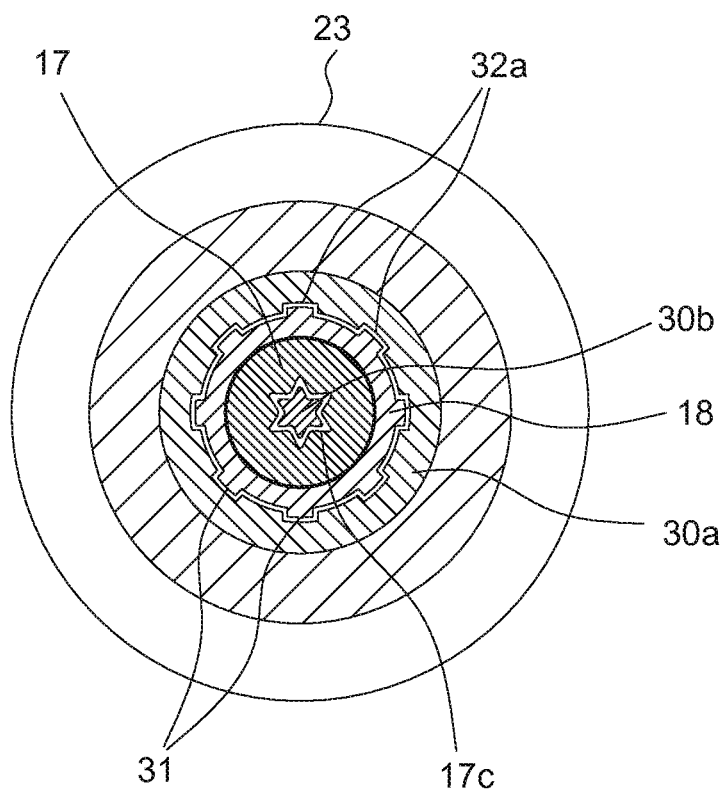
FIG. 11 is a section through the device with inserted inhaler along the line XI-XI of FIG. 10.

FIGS. 9 to 11 show the inhaler 1 and the device 23 with the inhaler 1 according to a further embodiment. In FIG. 10 parts of the inhaler 1 which are covered by the device 23 when the inhaler 1 is inserted into the device 23 are shown in dashed lines. Hereinafter only the differences from the previously explained embodiments are described, and the above explanations preferably also apply to the embodiment of FIGS. 9 to 11.

The inhaler 1 according to the embodiment of FIGS. 9 to 11 is preferably constructed at least substantially identically and/or functions according to the same principle as the inhaler 1 according to the first embodiment. The inhaler 1 according to the embodiment of FIGS. 9 to 11 preferably differs in terms of a different design of the housing or the mechanical coupling to the device 3, from the inhaler 1 according to the previously described first embodiment.

In the embodiment of FIGS. 9 to 11 the inhaler 1 comprises a (lower) housing part 18, which by insertion into or coupling to the device 23 comes into engagement with the coupling device 30a in such a way that the inhaler 1 in or on the device 23 is or will be held securely to prevent rotation. This is explained in more detail below, in particular with the aid of FIG. 11. The lower housing part 18 can be formed in one piece with the housing part 16.

Furthermore, the device 23 preferably comprises a coupling device 30b, which when the inhaler 1 is inserted into or coupled to the inhaler 1 with the device 23, engages axially, preferably positively, in the inhaler 1, in particular in an inner housing part 17, and thereby produces a coupling via which energy can be added to the energy store 7 or the spring can be tensioned.

In particular this coupling is a plug-in coupling, which is realised automatically by inserting the inhaler 1 or coupling the inhaler 1 to the device 23, and via which energy can be added to the energy store 7 or the spring can be tensioned. In this way the device 23 preferably generates a turning movement, in particular as previously explained or with the drive 26, which in this case however is transmitted via the plug-in coupling to the inhaler 1, which in turn then tensions the spring.

In particular, a coupling of the drive 26 to parts of the inhaler 1 takes place via a plug-in coupling in such a way that the energy store 7 or the spring is compressed by a sliding block guide under movement of the container 3. Other solutions are however also conceivable here.

The plug-in coupling can be designed to be self-centring, so that on insertion of the inhaler 1 into the device 23 a counterpart arranged in the device 23 is accommodated in a self-centring manner in the housing part 18.

A plug-in coupling is understood to mean a preferably positive connection by axially inserting two parts having a common axis of rotation into one another, as a result of which a torque can be transmitted. However, the transmissibility of axial forces, transverse forces, bending moments or the like is not essential. In other words, it is a coupling for transmitting a torque from the device 23 to the inhaler 1 in such a way that energy can thereby be added to the energy store 7 or the spring can be tensioned. The torque-transmitting connection is preferably produced by inserting or coupling the inhaler 1 to the device 23.

A plug-in coupling can also be a shaft-hub connection.

The inhaler 1 according to the embodiment of FIGS. to 11 preferably comprises no coupling sections 31 or coupling sections deviating from the first embodiment. In the illustrated embodiment the coupling sections 31 are arranged exclusively on the lower housing part 18. In particular the housing part 18 here comprises more than two, preferably 6 or 8, coupling sections 31.

Preferably the inhaler 1 cannot be tensioned manually or exclusively by means of the device 23. It is therefore possible for the inhaler 1 to be designed in such a way that a manual tensioning of the inhaler 1 is not possible, or only with difficulty. This is achieved in particular in that the lower housing part 18 covers the inner housing part 17, that the lower housing part 18 cannot be removed, and/or that the inner housing part 17 cannot be gripped and/or turned with the fingers, or only with difficulty.

The device 23 is preferably designed so that on insertion of the inhaler 1, the first coupling device 30a engages in the coupling sections 31 of the housing part 18 and/or vice versa, so that the inhaler 1 and/or the housing part 18 is held in a rotation-proof manner.

In particular, in the embodiment of the inhaler 1 shown in FIGS. 9 to 11, in contrast to the previously described embodiments the lower housing part 18 is not coupled or cannot be coupled in a rotation-proof manner to the inner part 17, but can be twisted or rotated with respect to the inner part 17.

Preferably the housing part 17 of the inhaler 1 is designed so that with the device 23 or its (second) coupling device 30b it can be engaged in the inhaler 1, in particular from below or from the underside of the inhaler 1, whereby a mechanical coupling takes place.

The second coupling device 30b is therefore preferably designed for coupling to the inner housing part 17, in particular by axial engagement in the housing part 17 from below.

In particular, a (direct) rotation-proof fixed coupling of the second coupling device 30b of the device 23 to the rotatable inner part 17 of the inhaler 1 is thus possible, so that the inhaler 1 can be tensioned by means of the device 23. Accordingly the coupling device 30a for the inhaler 1 is not formed on an upper edge 33 of the receptacle 25. Instead, the coupling device 30a for the inhaler 1 is designed in such a way that the inhaler 1 or its lower housing part 18 can be positively connected or coupled to the coupling device 30a. Accordingly, the recesses 32a of the coupling device 30a can also be omitted or can be configured differently than in the first embodiment (as recognisable in FIG. 11). In particular, this results in a lower overall height of the device 23 compared to the first embodiment.

FIG. 11 shows a section through the device 23 with the inhaler 1 inserted therein, along the section line XI-XI shown in FIG. 10.

The first coupling device 30a is preferably designed ring-shaped and/or includes the inhaler 1 or its housing part 18 inserted into the device 23.

The inner part or inner housing part 17 can preferably be rotated relative to the housing part 18.

The housing part 17 preferably comprises a coupling receptacle 17c for the coupling, in particular rotation-proof, of the housing part 17 to the (second) coupling device 30b of the device 23. The coupling receptacle 17c is preferably arranged on an underside of the housing part 17 and/or centrally or centrically, in particular symmetrically to the axis of rotation D. The coupling receptacle 17c is preferably open downwardly or preferably forms a downwardly open depression or opening of the housing part 17.

The coupling receptacle 17c or the thereby formed opening is preferably so small that the coupling receptacle 17c cannot be engaged by hand or by fingers, so that a manual rotation of the housing part 17 by a user (not shown) is prevented or at least is made much more difficult. Preferably the inhaler 1 according to the embodiment shown in FIGS. 9 to 11 cannot be tensioned manually, or can be tensioned only by means of the device 23. Faulty operations can thus be avoided.

The coupling receptacle 17c is preferably designed corresponding or complementary to the coupling device 30b. In the illustrated example the coupling receptacle 17c is star-shaped. However, other solutions are also possible here, for example a hexagonal or square shape or other configurations suitable for the rotation-proof coupling.

Accordingly the coupling device 30b is preferably designed corresponding to the coupling receptacle 17c, in particular also in a star shape, hexagonal or square shape.

The (second) coupling device 30b is preferably arranged centrically or centrally, in particular along the axis of rotation D, in the device 23 or the receptacle 25. Particularly preferably the coupling device 30b projects axially in the direction of the axis of rotation D or upwardly from the base 25a of the receptacle 25. In particular the coupling device 30b is designed like a pin or nipple.

In this solution the inhaler 1 is thus also coupled to the device by axial insertion. On insertion, the first coupling device 30a is positively coupled to the housing part 18, whereby radially projecting coupling sections 31 arranged in the circumferential direction on the housing part 18 engage with associated recesses 32a of the coupling device 30a. On insertion, the second coupling device 30b is also coupled to the inner housing part 17, wherein the pin-like coupling device 30b is introduced by insertion from below into the coupling receptacle 17c or the inhaler 1 is introduced from above onto the pin-like coupling device 30b. As described in more detail above in the first embodiment, a tensioning of the inhaler 1 or addition of energy to the energy store 7 can then take place by rotating the housing parts 17 and 18 relative to one another.

In a further embodiment, not shown, the inhaler 1 can—particularly in addition to one or more of the hitherto discussed features and aspects—be designed so that it is triggered by a user or patient breathing in or inhaling. In other words, the inhaler 1 can thus be designed so as to trigger breathing. In particular manual triggering by actuating the triggering push button 8a can thereby be omitted.

In this further embodiment the inhaler 1 preferably comprises a detection means for detecting an air flow, in particular a breathing in or an inhalation, and/or a triggering means for triggering the delivery of a corresponding dose.

Preferably the detection means comprises a sensor for detecting a pressure, a pressure drop, a velocity, an increase in velocity or a value which is associated with an air flow through the inhaler 1, in particular through the mouthpiece 13, when the patient breathes in.

The corresponding detection signal indicating breathing in by a patient can be used by the triggering means to trigger a delivery of a corresponding dose. In other words, the inhaler 1 can be triggered automatically by or on detection, or can be configured for this purpose.

In particular the triggering means can be coupled to the pressure generator 5 in such a way that a dose is delivered with the pressure generator 5 if a signal is detected.

The triggering means can for example operate electrically, electronically, pneumatically and/or mechanically.

In particular, a breathing trigger can be realised with the detection means and/or with the triggering means. The breathing trigger serves preferably for triggering based on an inhalation through the inhaler 1 or by an air flow initiated by the inhaler 1.

The detection means and/or the triggering means can include a valve that is opened by an air draught, in particular during inhalation. The opening of the valve can then be detected mechanically and/or electrically for example, so that a dose is delivered following the detection. Instead of the valve, a flap or a membrane can also be provided.

In particular it can be envisaged that a valve, flap and/or membrane are mechanically coupled to the pressure generator 5 in such a way that a dose is delivered or the aerosol 14 is generated by an inhalation. Alternatively or additionally, an electronic solution is however also conceivable. For example, a pressure sensor can be provided, so that a delivery of a dose or generation of the aerosol 14 takes place or is effected when an inhalation is recorded or measured with the pressure sensor.

The communication device 37b of the inhaler 1 can be designed to receive signals from the detection means and/or triggering means, and in particular to relay them to the communication device 37a of the device 23.

In particular, the inhaler 1 is put into the triggering-ready state only depending on the use of the inhaler 1 that is detected with the detection means. For example, it is possible that a (renewed) putting of the inhaler 1 into the triggering-ready state only takes place when a previous use of the inhaler 1 has been detected by means of the detection means. Another possibility is that the inhaler 1 is not put into the triggering-ready state if a use of the inhaler 1 was detected with the detection means, for example if a pre-set or predetermined number of intended uses of the inhaler 1, for example a maximum daily dose, has already been achieved.

Preferably, the possibility of triggering by breathing in combined with the automatic setting to the trigger-ready state by means of the device 23 enables a particularly simple operation or use of the inhaler 1. In particular, neither a manual preparation of the inhaler 1 for the triggering nor a manual triggering is necessary, but instead the inhaler can be removed from the device 23, the triggering takes place automatically on breathing in, and the inhaler is then reinserted into the device 23. A use of the inhaler is thus conceivably designed to be simple and virtually fail-safe.

Individual aspects and features of the present invention can be implemented independently of one another, but also in any arbitrary combination with one another.

List of reference numerals:

| | |
|---|---|
| 1 | inhaler |
| 2 | fluid |
| 3 | container |
| 4 | fluid space |
| 5 | pressure generator |
| 6 | holder |
| 7 | energy store |
| 8 | locking element |
| 8a | triggering push button |
| 9 | delivery tube |
| 10 | non-return valve |
| 11 | pressure chamber |
| 12 | discharge nozzle |
| 13 | mouthpiece |
| 14 | aerosol |
| 15 | supply air opening |
| 16 | housing part |
| 16a | flat portions |
| 17 | inner part |
| 17a | upper part (inner part) |
| 17b | lower part (inner part) |
| 17c | coupling receptacle |
| 18 | (lower) housing part |
| 19 | holding element |
| 20 | spring |
| 21 | container base |
| 22 | piercing element |
| 23 | device |
| 24 | standing surface |
| 25 | receptacle |
| 25a | base |
| 26 | drive |
| 27 | motor |
| 28 | gear mechanism |
| 29a | (first) gearwheel |
| 29b | (second) gearwheel |
| 30a | coupling device |
| 30b | coupling device |
| 31 | coupling section |
| 32a | recess |
| 32b | recess |
| 33 | edge |
| 34 | teeth |
| 35 | sensor |
| 36 | controller |
| 37a | communication device (device) |
| 37b | communication device (inhaler) |
| 38 | external system |
| 39a | data connection |
| 39b | data connection |
| 40 | counter |
| 41 | dispenser |
| 42 | energy supply device |
| 43 | energy store |
| 44 | charging device |
| D | axis of rotation |

The invention claimed is:

1. A device (23) for putting an inhaler (1) into a triggering-ready state by adding mechanical energy to an energy store (7) of the inhaler (1), the device being configured for mechanically coupling to an end portion of the inhaler in order to put the inhaler into the triggering-ready state, the device being sized so that an opposite end portion of the inhaler is located out of the device in a mechanically coupled state, the device (23) comprising:
a motor drive (26) configured to provide relative movement of two housing parts (16, 17, 18) of the inhaler (1) with respect to one another in said mechanically coupled state,
wherein by the movement of the housing parts (16, 17, 18) relative to one another by said motor drive, the mechanical energy is added to the energy store (7), and
wherein the device (23) is configured to be portable and manually transportable by a patient by hand without aids, and wherein the device is configured to be manually lifted and brought to the patient's mouth for inhalation by the patient in said mechanically coupled state.

2. The device according to claim 1, further comprising: two coupling devices (30a, 30b),
wherein the coupling devices (30a, 30b) are each mechanically coupled to one of two housing parts (16, 17, 18) of the inhaler (1) so that the two housing parts (16, 17, 18) are movable relative to one another via the coupling devices (30a, 30b), and
wherein movement of the housing parts (16, 17, 18) relative to one another causes mechanical energy to be added to the energy store (7) of the inhaler (1).

3. The device according to claim 1, wherein the drive (26) operates to rotate the housing parts (16, 17, 18) relative to one another by at least one of: (i) more than 90°; (ii) at most 360°; and (iii) 180°.

4. The device according to claim 1, further comprising means for stopping an addition of mechanical energy to the energy store (7) when a predetermined maximum torque of the drive is reached, wherein the maximum torque is at least one of: (i) 0.5 Nm, (ii) 0.6 Nm, and (iii) 0.8 Nm.

5. The device according to claim 1, wherein the drive (26) comprises an electric motor (27) and/or a gear mechanism (28).

6. The device according to claim 1, wherein the device (23) comprises a sensor (35), which is designed to detect the insertion, coupling and/or a state or tension state of the inhaler (1).

7. The device according to claim 6, wherein the device (23) comprises a controller (36), which is designed to detect with the sensor (35) the insertion and/or coupling of the inhaler (1) and the state or the tension state, and depending thereon, to control the drive (26) so that the inhaler (1) is automatically put into the triggering-ready state by addition of the mechanical energy to the energy store (7).

8. The device according to claim 1, wherein the device (23) comprises a communication device (37a) for communication with the inhaler (1) and/or an external system (38), wherein the communication device (37a) is designed to send and/or receive information on a state of the inhaler (1) and/or its use.

9. The device according to claim 1, wherein the device (23) comprises an electronically operated output device (41) for optical and/or acoustic output of information on a condition of the inhaler (1) and/or its use.

10. The device according to claim 1, wherein the device (23) comprises an energy supply device (42) for supplying the device (23) with energy and/or a charging device (44) for charging an energy store (43) of the Inhaler (1).

11. The device according to claim 1, wherein at least one of:
the device (23) comprises a receptacle (25) for the insertion and/or retention of the inhaler (1), and
the device (23) is designed so that by inserting the inhaler (1) into the receptacle (25), the drive (26) is connected to one of the housing parts (16, 17, 18) and the other housing part (16, 17, 18) is positively connected to the receptacle (25), so that the housing part (16, 17, 18) connected to the drive (26) is rotatably movable relative to the other housing part (16, 17, 18), and the other housing part (16, 17, 18) is held, at least during tensioning, immovably, in a rotation-proof manner, in the receptacle (25).

12. The device according to claim 1, wherein the device (23) is designed as a docking station and/or charging station for the inhaler (1).

13. The device according to claim 1, wherein the device (23) comprises a communication device (37a) for the wireless communication with an external system (38) and/or with a communication device (37b) of the inhaler (1).

14. The device according to claim 1, wherein the device (23) is designed as a compliance interface and/or serves for patient monitoring, patient supervision, dose monitoring and/or treatment supervision.

15. A system, comprising:
an inhaler (1) having an energy store (7); and
a device (23) for putting the inhaler (1) into a triggering-ready state by adding mechanical energy to the energy store (7) of the inhaler (1),
the device being configured for mechanically coupling to an end portion of the inhaler (1) in order to put the inhaler (1) into the triggering-ready state, an opposite end portion of the inhaler being located out of the device in a mechanically coupled state; and
a motor drive (26) configured to provide relative movement of two housing parts (16, 17, 18) of the inhaler (1) with respect to one another,
wherein by the movement of the housing parts (16, 17, 18) relative to one another the mechanical energy is added to the energy store (7), and
wherein the device (23) is configured to be portable and manually transportable by a patient by hand without aids, and wherein the device with the inhaler (1) is configured to be manually lifted and brought to the patient's mouth for inhalation together with the inhaler (1) by the patient.

16. The system according to claim 15, wherein the inhaler (1) comprises a counter (40) for counting uses of the inhaler (1).

17. The system according to claim 16, wherein the device (23) and the inhaler (1) each comprise a communication device (37a, 37b) for communication, so that a data connection (39b) can be established between the communication devices (37a, 37b) of the device (23) and the inhaler (1), and wherein the counter (40) has a data connection for sending data to one of the communication devices (37a, 37b).

18. The system according to claim 15, wherein the inhaler (1) comprises a mechanical pressure generator (5) for conveying and atomising a fluid (2), wherein the fluid (2) on addition of energy to the energy store (7) is conveyed to a pressure chamber (11) of the pressure generator (5), and/or wherein by detensioning the energy store (7) the fluid (2) is pressurised and is discharged via a discharge nozzle (12) as an inhalable aerosol (14).

19. The system according to claim 15, further comprising: two coupling devices (30a, 30b),
wherein the coupling devices (30a, 30b) are each mechanically coupled to one of two housing parts (16, 17, 18) of the inhaler (1) so that the two housing parts (16, 17, 18) are movable relative to one another via the coupling devices (30a, 30b), and wherein movement of the housing parts (16, 17, 18) relative to one another causes mechanical energy to be added to the energy store (7) of the inhaler (1).

* * * * *